(12) United States Patent
Rivera et al.

(10) Patent No.: US 10,106,572 B1
(45) Date of Patent: Oct. 23, 2018

(54) SUPRAMOLECULAR HACKY SACKS (SHS), METHOD OF SYNTHESIS AND APPLICATIONS THEREOF

(71) Applicants: Jose M Rivera, San Juan, PR (US); Luis M Negron, Corozal, PR (US)

(72) Inventors: Jose M Rivera, San Juan, PR (US); Luis M Negron, Corozal, PR (US)

(73) Assignee: University of Puerto Rico, San Juan, PR (US)

( * ) Notice: Subject to any disclaimer, the term of this patent is extended or adjusted under 35 U.S.C. 154(b) by 0 days.

(21) Appl. No.: 14/791,360

(22) Filed: Jul. 3, 2015

Related U.S. Application Data

(60) Provisional application No. 62/020,589, filed on Jul. 3, 2014.

(51) Int. Cl.
*C07H 19/16* (2006.01)
*A61K 47/48* (2006.01)
*A61K 47/26* (2006.01)

(52) U.S. Cl.
CPC ....... *C07H 19/16* (2013.01); *A61K 47/48092* (2013.01); *A61K 47/48961* (2013.01)

(58) Field of Classification Search
None
See application file for complete search history.

(56) References Cited

PUBLICATIONS

Drug encapsulation studies with microglobules made from pH-responsive supramolecular G-quadruplexes, presented Apr. 8, 2013 at the 245th ACS National Meeting and Exposition, New Orleans, Louisiana.*

Supramolecular pH-responsive G-quadruplexes, presented Apr. 10, 2013 at the 245th ACS National Meeting and Exposition, New Orleans, Louisiana.*

* cited by examiner

*Primary Examiner* — Layla D Berry
(74) *Attorney, Agent, or Firm* — Hoglund & Pamias, PSC; Roberto J. Rios

(57) ABSTRACT

The invention is directed to small molecules that self-assemble hierarchically to form NPs termed SHS (due to their architectural features). These SHS are composed by precise supramolecules known as Supramolecular G-Quadruplexes (SGQs) which are formed when amphiphilic guanosine (G) derivatives that self-assemble in presence of salt by non-covalent interactions. The resulting SGQs are made of amphiphilic guanosine (G) subunits (with precisely eight subunits at neutral pH (pH>5.7) or sixteen subunits at acidic pH (pH<5.7)). The SGQs are responsive entities that further self-assemble upon an external stimulus, such as an increase in temperature or a change in pH, leading to the formation of the aforementioned SHS.

36 Claims, 33 Drawing Sheets

(E)-3-(1-methyl-1H-imidazol-2-yl)-1-phenylprop-2-en-1-one (ImAG std)

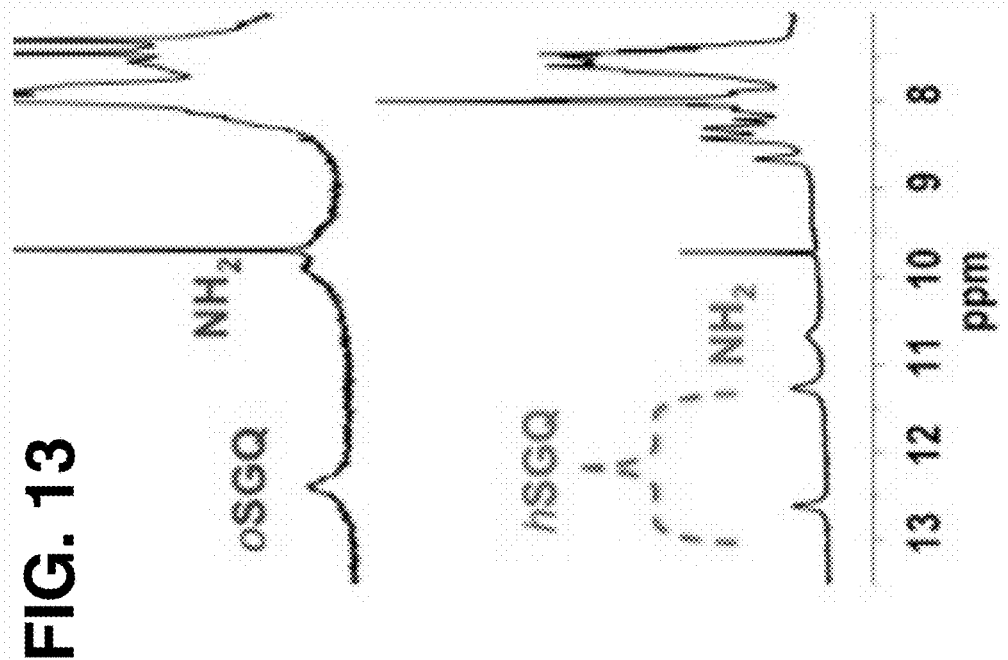
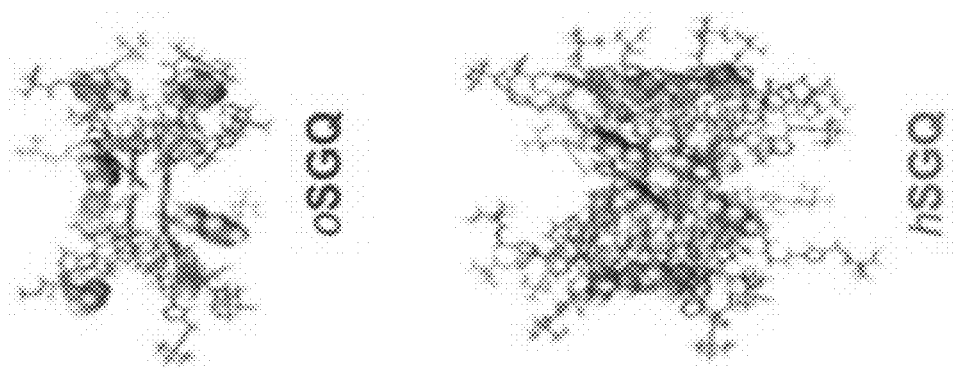
FIG. 13

SUPRAMOLECULAR HACKY SACKS (SHS), METHOD OF SYNTHESIS AND APPLICATIONS THEREOF

GOVERNMENT INTEREST

The claimed invention was made with U.S. Government support under grant numbers GM-093994 and GM-061151 awarded by the National Institutes of Health (NIH). The government has certain rights in this invention.

BACKGROUND OF THE INVENTION

The approval of new drugs have slowed down significantly in the last couple of decades, not because of a slow down in the discovery of new therapeutic agents (e.g., small molecule drugs, proteins) with good activity in vitro (good pharmacodynamics), but because most of those new agents have poor efficacy in vivo (poor pharmacokinetics) in humans. Out of more than 6,000 new molecules synthesized in the pharmaceutical industry, only one gains FDA approval to be used in the clinic and only one in twenty drug candidates that make it to clinical trials reaches the market. To make matters worse, it takes longer than a decade to develop a promising drug candidate and the expense of doing so has been estimated to reach up to $1 billion. Faced with this situation, most pharmaceutical companies decide to narrow their focus towards diseases that afflict only large segments of the population, leaving many other human diseases untreated. There is a critical need to solve this problem in order to improve human health and quality of life. A number of potential solutions have been proposed, including making and screening even larger libraries of compounds and using novel therapeutic agents (e.g., proteins, DNA and RNA) for alternative treatment strategies (e.g., gene delivery, interfering-RNA). Those strategies, however, will face similar obstacles to small-molecule based drugs, which is, unacceptable in vivo efficacy due to poor pharmacokinetics. One of the most promising strategies to overcome this problem, however, relies on the use of nanoparticles (NPs) as Drug Delivery Systems (DDS). The field of nanoparticle-based drug delivery systems (NP-DDS) is vast and with a relatively long history spanning more than four decades. We describe NPs, with a size less than 10 μm, in the context of systems with the capability to contain or encapsulate from a variety of guest small molecules to complex macromolecules by protecting them from the outer environment (e.g., physiological conditions). By protecting the encapsulated cargo from the surroundings, NPs can be targeted as a DDS to a current tissue with a specific disease. A number of such DDS are already used in the clinic to treat diseases such as cancer, while others are currently undergoing clinical trials. The most successful DDS to date rely on nanoparticles based on lipids (LNP) and polymers (PNP) have continued to be used as DDS.

Although such LNPs and PNPs are indeed providing steady progress towards improving drug efficacy, they have certain limitations. LNPs tend to be unstable during dilution (e.g., upon administration), which lead to leakage of the encapsulated drug. PNPs have overcome many of the limitations of LNPs, but they suffer from other issues such as polydispersity (i.e., a distribution of molecules of similar but not identical properties), which become more prevalent upon scaling up their synthesis, making it difficult to obtain the high purity and reproducibility required to make clinically grade materials. However, such limitations regarding scaling up in synthesis, purification and reproducibility could be overcome by exploring the use of small molecules. Despite all the work done in the field, to the best of our knowledge (and besides lipids), there are no examples of small-molecule NP-DDS.

A convenient way to develop small-molecule NP-DDS is the use of supramolecular chemistry, which enhances the construction of complex chemical systems performed via non-covalent interactions (e.g., hydrogen bonds, π-π interactions, metal coordination, ion pairing, hydrophobic effects, van der Waals forces). In comparison with molecules that use atoms as building blocks by covalent bonds, in supramolecular systems, molecules are the building blocks of the resulting non-covalent assemblies. With the advantage of using supramolecular chemistry, we have been synthesizing hydrophilic 8-aryl-2'deoxyguanosine (8ArG) derivatives and studying their self-assembly in order to expand the current knowledge of the self-assembly of small molecules in aqueous media and to test the potential for the corresponding supramolecules to serve as self-assembled ligands for G-quadruplex DNA (QDNA). Guanosine is a naturally occurring recognition motif well known for its ability to pair with cytosine in both DNA and RNA structures. Guanosine is also self-complementary, which allows it to form planar cyclic tetrameric structures that further associate into coaxial stacks to form either supramolecular G-quadruplexes (SGQs, made from individual G subunits) or oligonucleotide G-quadruplexes (e.g., QDNA, QRNA). QDNA is the subject of intense studies due to its putative role in telomere function and in the regulation of some oncogenes.

This library of hydrophilic 8ArG derivatives, which have allowed us to deepen the fundamental knowledge of small molecule self-assembly in water, provided structural insights of the resulting supramolecular G-quadruplexes (SGQs). For example, we have developed the 8-meta-acetyl-guanosine (mAG) moiety into an attractive recognition motif to enable the construction of well-defined and discrete supramolecular nanostructures. We demonstrated this by using it to construct lipophilic hexadecameric self-assembled dendrimers (SADs). Our discovery that a positively charged hydrophilic mAG derivative self-assembles isostructurally into hexadecamers in aqueous media prompted us to explore the construction of congeneric hydrophilic SADs. In addition, we have developed ways to modulate the supramolecular properties such as molecularity, fidelity and stability (thermodynamic and kinetic). We have evaluated how changing parameters that are intrinsic (structure of the derivatives) and extrinsic (e.g., pH, temperature, concentration, cation template) to the SGQs alter their structure and dynamics.

While studying the self-assembly of some of the 8ArG derivatives described before, we discovered one particular derivative whose corresponding SGQ showed thermoresponsive behavior. We demonstrated that upon reaching a threshold temperature (Lower Critical Solution Temperature, LCST) these SGQs further self-assemble to form nano/micro hydrogel globules we termed supramolecular hacky sacks (SHS). The LCST is a phenomenon observed in amphiphilic systems that are soluble at one temperature, but once a transition temperature is reached, there is a volume phase transition that produces a change in the solvation state from random coil to globule (e.g., polymeric systems). This represented, to the best of our knowledge, the first example of thermoresponsive system made from a non-polymeric precise supramolecule. Such LCST phenomenon enables the construction of "smart" NP-DDS whose formation can be triggered by just increasing the temperature above its transition temperature.

These findings uncovered a new paradigm in the development of smart responsive materials with properties and applications similar to those of polymeric systems, but with the potential advantage of being based on small molecules. Since that initial discovery, we further reported these SHS to be suitable for encapsulating the anti-cancer drug doxorubicin and, more recently, we reported on ways to modulate the LCST by altering the distribution of hydrophobic patches on the surface of the SGQs. However, biorelevant applications of thermoresponsive materials are limited by the narrow window of physiological temperatures, which complicates their implementation.

Nevertheless, the human body has different regions (organs) that have different pH values (human tumors 5.7-7.8, endosome pH<6), making a pH stimulus a feasible strategy for the design of pH responsive materials for drug encapsulation, biosensors and other novel materials in biotechnology. Currently, in the field of pH-responsive materials, most reported systems are polymeric, such as micelles, liposomes, dendrimers, hydrogels, and others. Despite the increasing number of reported stimuli responsive polymeric materials and nanoparticles, there are still significant challenges that must be overcome, such as difficult synthetic protocols, cytotoxicity and complex modifications for biological recognition.

Self-assembly is a very convenient tool for the construction of pH-responsive supramolecular nanomaterials. Even though this method offers an advantage over conventional organic multistep synthesis, there are not many reported examples of non-polymeric pH-responsive materials. Even with the existence of many reported thermo- and pH-responsive systems that can self-assemble under a certain stimulus; there are still certain limitations regarding the precise modulation of the composition and structure of these materials.

SUMMARY OF THE INVENTION

After discovering non-polymeric 8ArG derivatives that are thermoresponsive hexadecameric supramolecular G-quadruplexes (SGQs), we redesigned the corresponding 8ArG derivative at the C8-position with an imidazole group in order to obtain a dual thermo- and pH-responsive SGQ. The imidazole moiety was chosen for the design of pH-responsive materials because it possesses a biologically relevant pKa value (pKa~6), it is non-toxic and exhibits fusogenic (fuse with membranes) behavior in cellular membranes. This is a versatile non-polymeric thermo- and pH-responsive SGQ constructed from previously reported 8-(meta-acetylphenyl)-2'-deoxyguanosine (mAG) moiety with a simple Claisen-Schmidt condensation reaction, in which self-assembly can be precisely modulated to obtain well-defined nanoglobules. The SHS formed by these thermo/pH-responsive modified SGQs are suitable for the encapsulation and controlled release into biological systems of a broad spectrum of therapeutic agents (e.g., small molecule drugs, carbohydrates, proteins, DNA).

Accordingly, the present invention described here relates to small molecules that self-assemble hierarchically to form NPs that we termed SHS (due to their architectural features). These SHS are composed by precise supramolecules known as Supramolecular G-Quadruplexes (SGQs), which are formed when amphiphilic guanosine (G) derivatives self-assemble in presence of salt (e.g., KI) via non-covalent interactions. The resulting SGQs are made of amphiphilic guanosine (G) subunits (eight subunits at neutral pH (pH>5.7) and/or sixteen subunits at acidic pH (pH<5.7)).

The SGQs are responsive entities that further self-assemble upon an external stimulus, such as an increase in temperature or a change in pH, leading to the formation of the aforementioned SHS particles.

The present invention also provides a combination of many of the advantages of LNPs and PNPs with the particularly attractive feature of being based on small molecules that are easy to synthesize, can be optimized for specific biomedical applications via standard high throughput screening methods and could be produced in large scales at the purity required for clinical applications. Because of these reasons the present invention have a large potential to be successfully commercialized.

The present invention further provides a method of preparation that we termed fixing process protocol in which the SHS can tolerate extreme dilutions without affecting the NP globular gel-like integrity and composition. The fixing process protocol requires no stabilizers or post-modifications like the use of covalent cross-linking agents to tolerate dilutions. This protocol can also be used to wash the SHS with an encapsulated guest or cargo like a therapeutic agent (e.g., small molecules, carbohydrates, polymers, proteins, DNA), without losing significant amounts of encapsulated cargo that can be detected in the exterior aqueous media outside the SHS. This is a convenient way to remove non-encapsulated cargo and dilute the SHS to work with living systems under physiological conditions.

According to another aspect of the invention, the SHS composed of a pH/thermo-responsive SGQ, which are formed by G subunits containing an imidazole moiety, includes an act of providing a suitable delivery/release method in which the SHS can be internalized in some cell lines such as SH-SY5Y (neuroblastoma) and HEK-293 (human embrionic kidney cells). The encapsulated guest can be released by a change in pH in the environment in which the SHS is disassembled at acidic pH completely releasing the guest. According to yet another aspect of the invention, a release method is the controlled release in which the encapsulated guest is slowly released as a function of time. The fact that such broad spectrum of biorelevant molecules can be encapsulated and released by these alternative methods opens the door to multiple applications in drug and gene delivery for clinical applications.

BRIEF DESCRIPTION OF THE DRAWINGS

Further features and advantages of the invention will become apparent from the following detailed description taken in conjunction with the accompanying figure showing illustrative embodiments of the invention, in which:

FIG. 13 shows $^1$H NMR for ImAGpD2OH at pH 5 (below) and at pH 7 (above), according to an embodiment of the present invention.

DETAILED DESCRIPTION OF THE INVENTION

Figure 1:
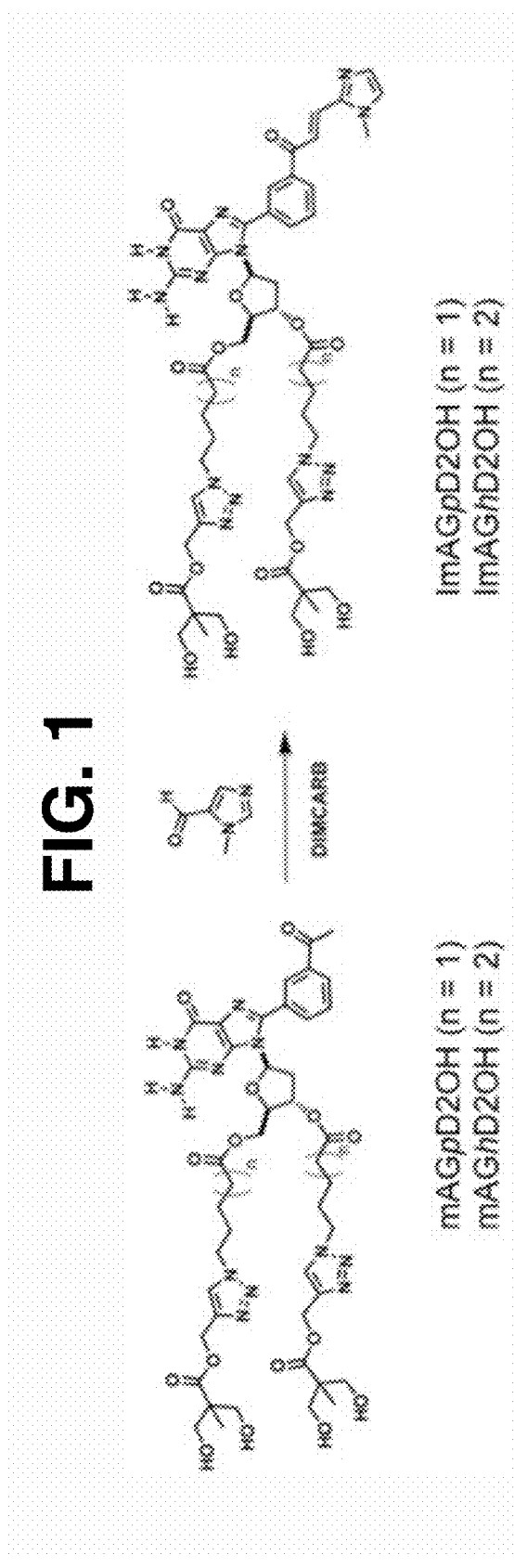
FIG. 1 shows the synthetic scheme for the preparation of ImAGpD2OH and ImAGhD2OH by a Claisen-Schmidt condensation, according to an embodiment of the present invention.

The present invention is directed to 8ArG derivatives that self-assemble in thermoresponsive SGQs and that also respond to pH as an alternative stimulus. FIG. 1 describes the preparation of imidazole-functionalized 8ArG derivatives constructed from acetyl phenyl moiety in the C8 position that now will be the starting material for the novel pH-responsive SGQ derivatives. To add the imidazole functionality to mAGpD2OH and mAGhD2OH, a Claisen-Schmidt condensation was performed with a commercially available imidazole aldehyde (1-methyl-1H-imidazole-2-carbaldehyde). Preliminary attempts to perform an aldol condensation with KOH were not successful since there were significant amounts of impurities leading to a lower yield relative to the Claisen-Schmidt condensation using DIMCARB. Also, the KOH have strong basic conditions that can affect the ester groups of the 5' and 3' of the ribose in the 8ArG. Using DIMCARB provides a cleaner reaction and the final product can be purified by a simple wash with organic solvents. This is a versatile reaction that expands the current library of 8ArG derivatives to include a wide variety of functional groups. One advantage of this method is that the functionality is added in the last step of the synthesis without affecting the desired group (e.g., imidazole).

Procedure for the Preparation of ImAGhD2OH, ImAGpD2OH and ImAG Standard

Figure 2:
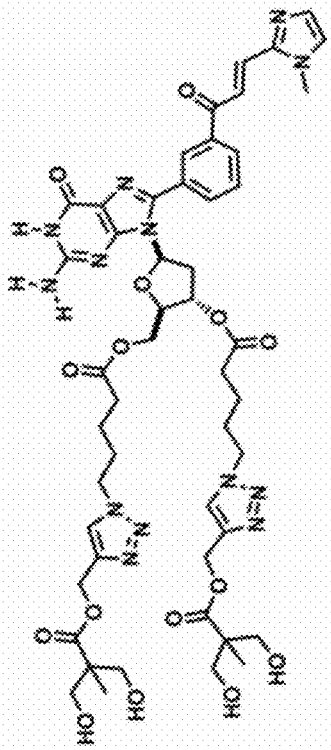
FIG. 2 shows the molecular structure of ImAGhD2OH, according to an embodiment of the present invention.
Figure 3:
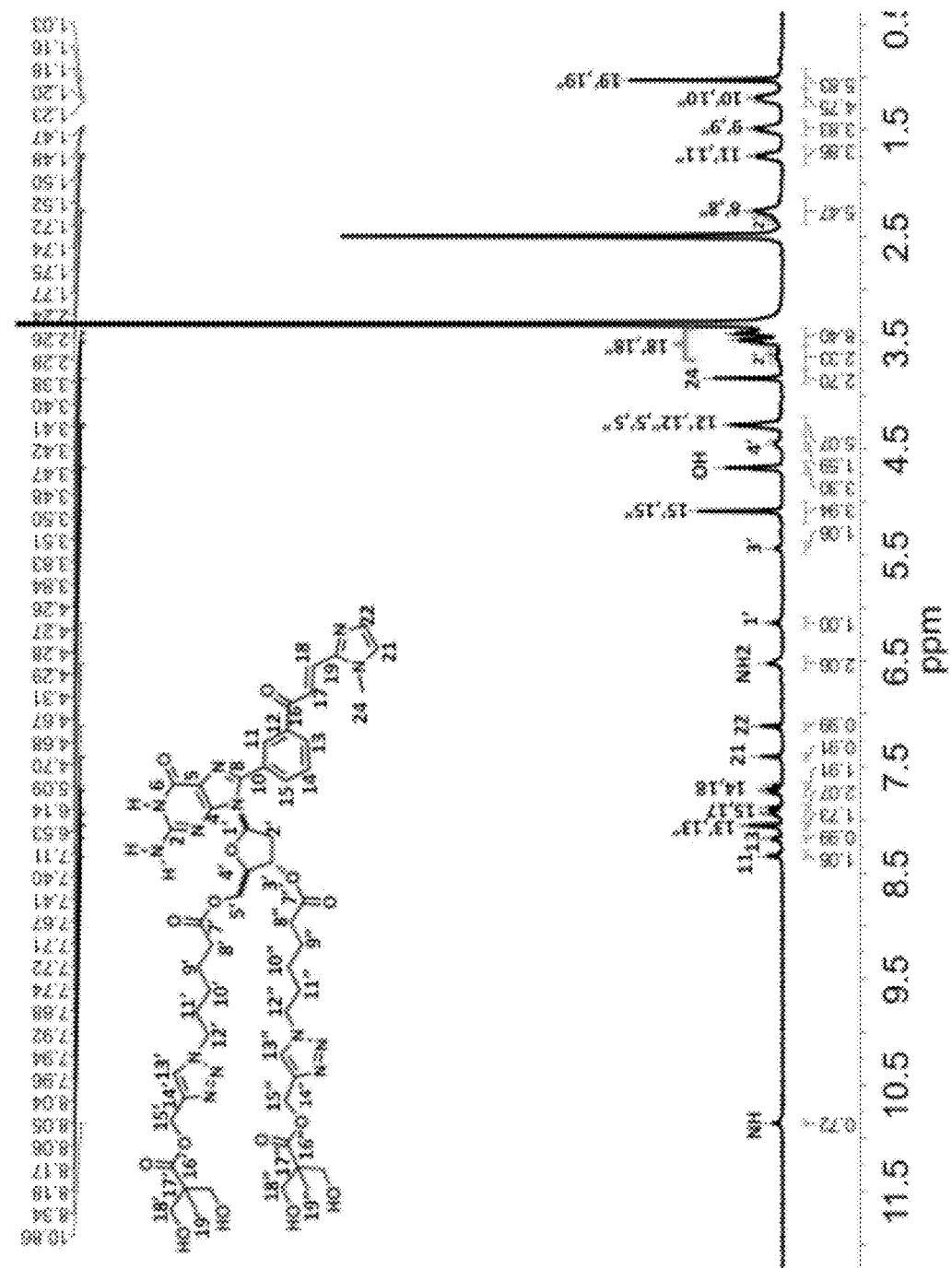
FIG. 3 shows $^1$H NMR of ImAGhD2OH, according to an embodiment of the present invention.
Figure 4:
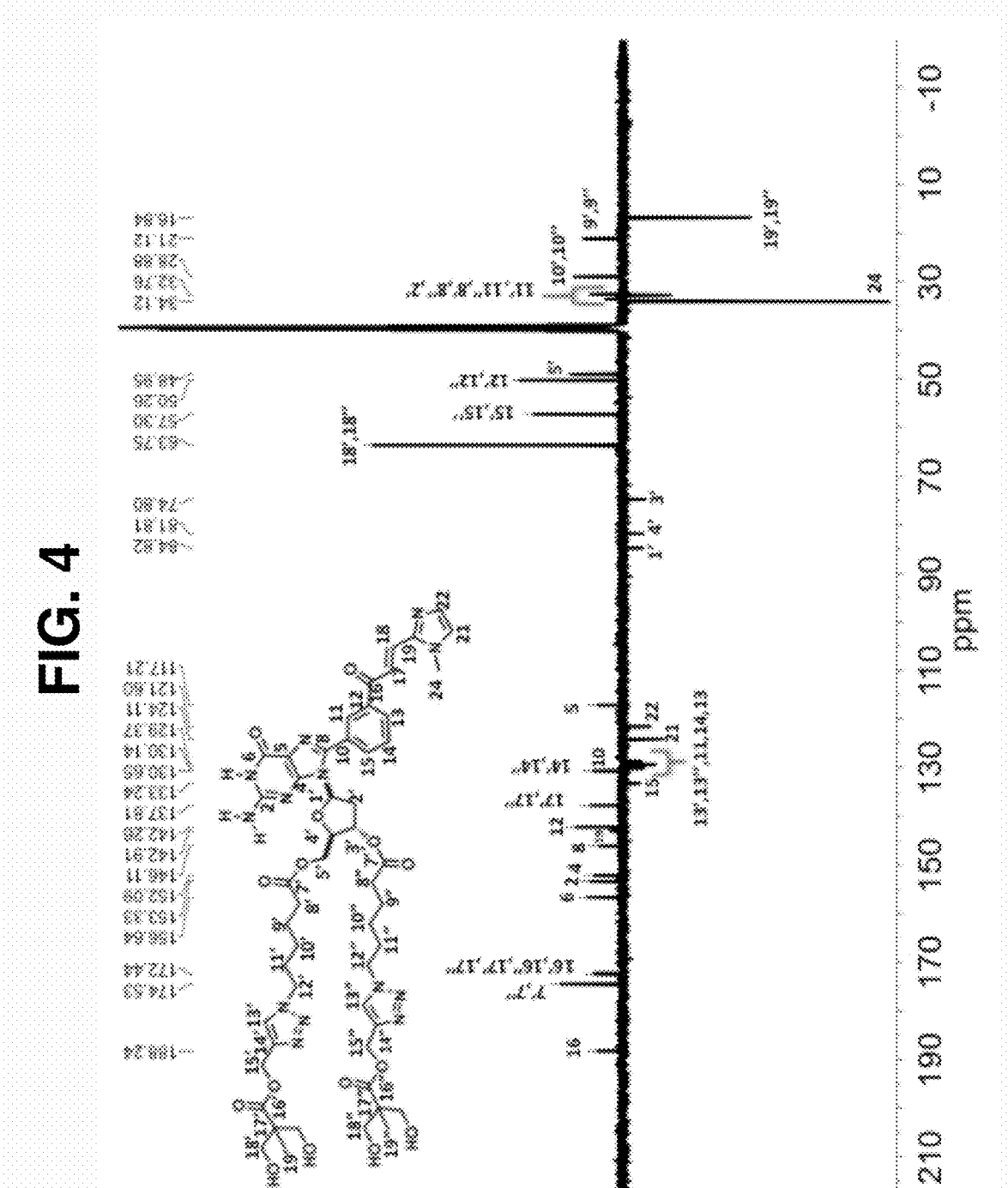
FIG. 4 shows $^{13}$C NMR of ImAGhD2OH, according to an embodiment of the present invention.

FIG. 1 shows the synthetic scheme for the preparation of ImAGpD2OH and ImAGhD2OH by a Claisen-Schmidt condensation, where n represents the amount of $CH_2$ groups of the 5' and 3' of the ribose in the 8ArG. mAGhD2OH was synthesized from previously reported procedures (the same reported procedure was used also for the synthesis of mAGpD2OH). After 1 day drying in vacuum, mAGhD2OH (50 mg, 0.05 mmol) was dissolved in 1 mL of Dimethyl-ammonium dimethylcarbamate (DIMCARB) for 10 minutes. After the entire solid was dissolved in DIMCARB, 1-methyl-1H-imidazole-2-carbaldehyde (12.5 mg, 0.1 mmol) was added. The reaction was monitored by TLC (EtOAc:MeOH, 8:2), in order to determine when the mAGhD2OH was consumed. After 48 h, the reaction was quenched by neutralization of DIMCARB with HCl 10%. After neutralization, a yellow precipitate was obtained by decantation. This solid was left in vacuum for h. The yellow solid, ImAGhD2OH (with a molecular structure as shown in FIG. 2) was washed with dry DCM, ether and hexane then lyophilized. ImAGhD2OH, with a chemical formula $C_{51}H_{65}N_{13}O_{15}$, was characterized as shown in FIG. 3 and FIG. 4 by using $^{1}H$ NMR and $^{13}C$ NMR, respectively. Yellow solid, mp (121.4-124.5) ° C. TLC (EtOAc:MeOH, 7:3): $R_F=0$; 70% yield. $^{1}H$ NMR (500 MHz, DMSO-$d_6$): δ 10.86 (s, 1H), 8.34 (s, 1H), 8.19 (d, J=7.62 Hz, 1H), 8.06 (s, 2H), 8.06 (d, J=8.3 Hz, 1H), 7.92 (d, J=14.76 Hz, 1H), 7.74 (t, J=7.64 Hz, 1H), 7.71 (d, J=14.92 Hz, 1H), 7.41 (d, J=3.64 Hz, 1H), 7.14 (d, J=9.46 Hz, 1H), 6.53 (br-s, 2H), 6.15 (t, J=6.79 Hz, 1H), 5.44 (m, 1H), 5.09 (s, 4H), 4.68 (s, 3H), 4.48 (m, 2H), 4.31 (m, 6H), 3.84 (s, 3H), 3.65 (m, 1H), 3.51 (dd, J=5.32, 10.35 Hz, 8H), 2.38 (m, 1H), 2.28 (m, 4H), 1.78 (m, 4H), 1.52 (m, 4H), 1.23 (m, 4H), 1.03 (s, 6H). $^{13}C$ NMR (126 MHz, DMSO-$d_6$): δ 188.24, 174.53, 172.44, 156.64, 153.33, 152.09, 146.11, 142.91, 142.26, 137.81, 133.24, 130.65, 130.14, 129.54, 129.37, 128.98, 128.77, 124.11, 121.60, 117.21, 84.82, 81.81, 74.80, 63.75, 57.30, 50.26, 48.95, 34.12, 32.76, 28.88, 21.12, 16.84. ($v_{max}/cm^{-1}$): 3323, 2932, 2855, 2770, 2448, 2199, 2058, 1913, 1894, 1762, 1686, 1651, 1630, 1599, 1578, 1531, 1512, 1465, 1278, 1024. ESI-MS $[M+Na]^+$ 1122.2504 m/z.

Figure 5:
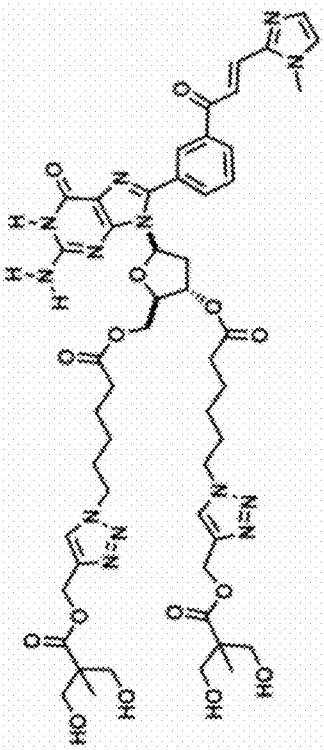
FIG. 5 shows the molecular structure of ImAGpD2OH, according to an embodiment of the present invention.
Figure 6:
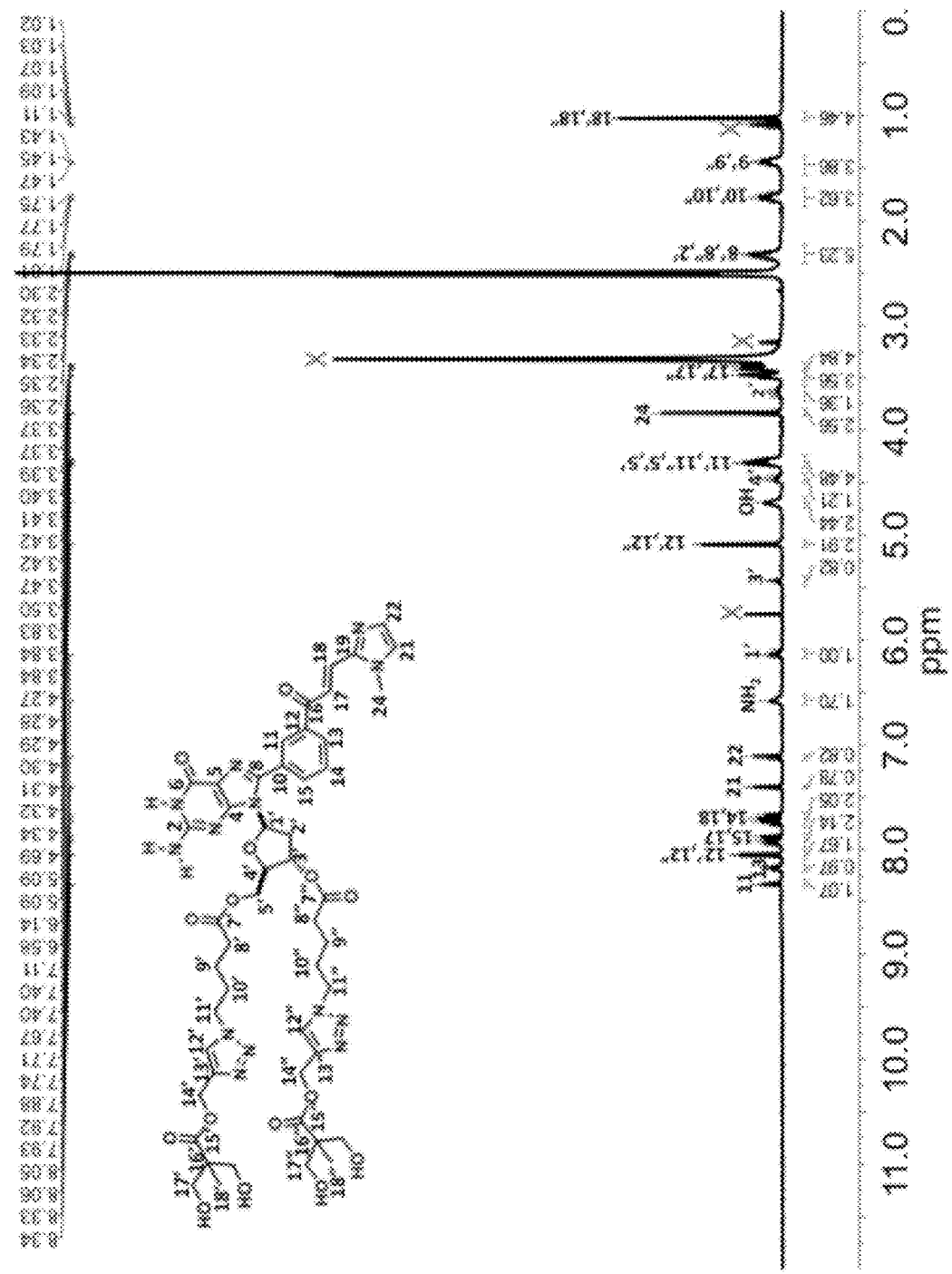
FIG. 6 shows $^1$H NMR of ImAGpD2OH, according to an embodiment of the present invention.
Figure 7:
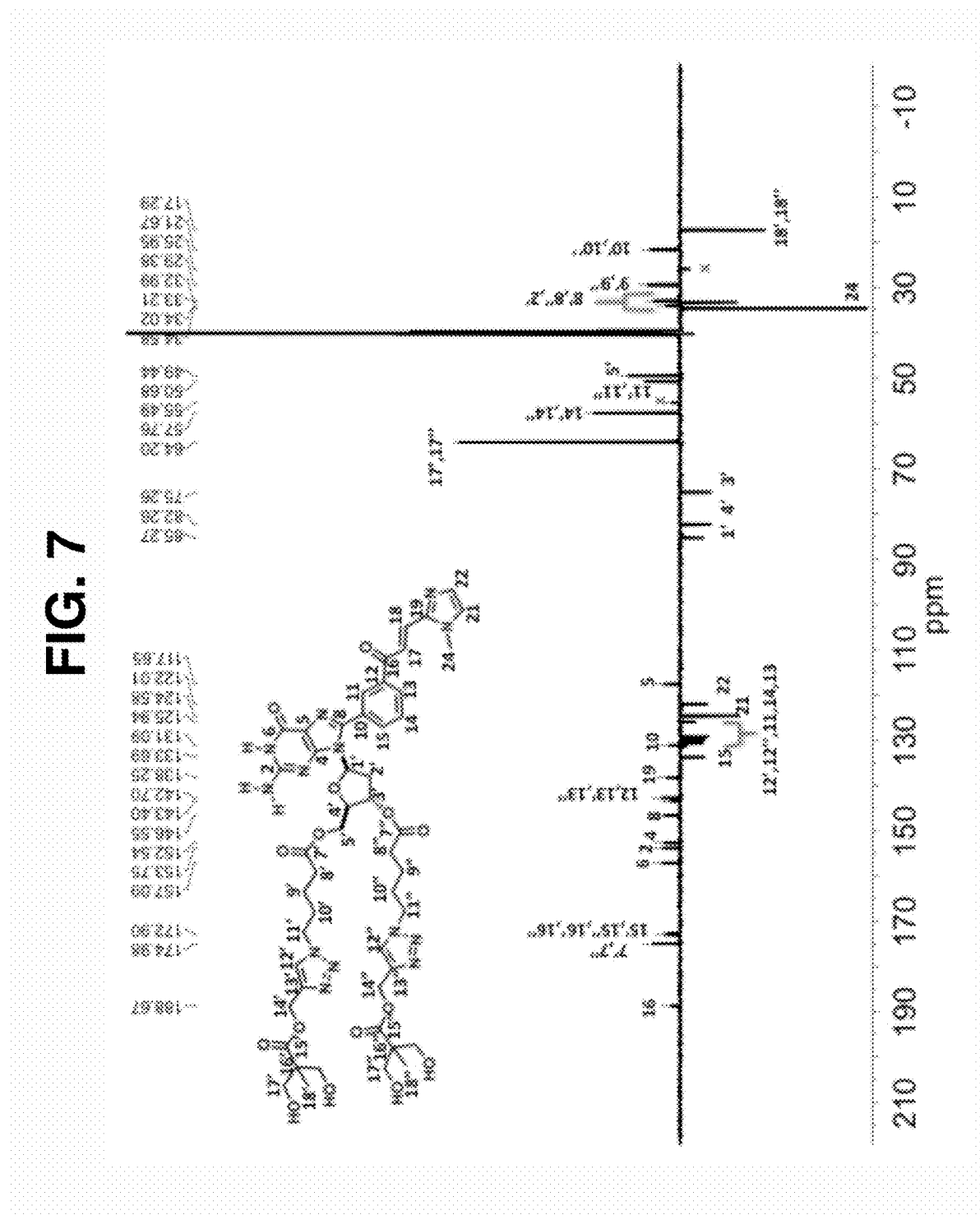
FIG. 7 shows $^{13}$C NMR of ImAGpD2OH, according to an embodiment of the present invention.

The same procedure explained above was applied with ImAGpD2OH (with a molecular structure as shown in FIG. 5). ImAGpD2OH, with a chemical formula $C_{49}H_{61}N_{13}O_{15}$, was characterized as shown in FIG. 6 and FIG. 7 by using $^{1}H$ NMR and $^{13}C$ NMR, respectively. Yellow solid, mp (80.2-83.6) ° C. TLC (EtOAc:MeOH, 7:3): $R_F=0$; 70% yield. $^{1}H$ NMR (500 MHz, DMSO-$d_6$): δ 8.34 (s, 1H), 8.33 (d, J=6.15 Hz, 1H), 8.06 (s, 2H), 8.06 (d, J=7.84 Hz, 1H), 7.93 (d, J=14.1 Hz, 1H), 7.74 (t, J=7.80 Hz, 1H), 7.67 (d, J=15.01 Hz, 1H), 7.40 (d, J=4.35 Hz, 1H), 7.11 (d, J=11.22 Hz, 1H), 6.58 (br-s, 2H), 6.14 (t, J=6.86 Hz, 1H), 5.44 (m, 1H), 5.09 (s, 4H), 4.69 (s, 3H), 4.46 (m, 2H), 4.32 (m, 6H), 3.84 (s, 3H), 3.50 (dd, J=5.30, 10.55 Hz, 8H), 2.36 (m, 1H), 2.30 (m, 4H), 1.79 (m, 4H), 1.47 (m, 4H), 1.02 (s, 6H). $^{13}C$ NMR (126 MHz, DMSO-$d_6$): δ 188.67, 174.98, 172.90, 157.09, 153.75, 152.54, 146.55, 143.40, 142.70, 138.25, 133.69, 131.09, 125.94, 124.58, 122.01, 117.65, 85.27, 82.26, 75.26, 64.20, 57.76, 50.88, 49.44, 34.58, 34.02, 33.21, 32.99, 29.38, 21.67, 17.29. ($v_{max}/cm^{-1}$): 3740, 3329, 3086, 3022, 2777, 2440, 1726, 1682, 1659, 1651, 1599, 1580, 1477, 1279, 1250, 1022. ESI-MS $[M]^+$ 1072.34 m/z.

Figure 8:
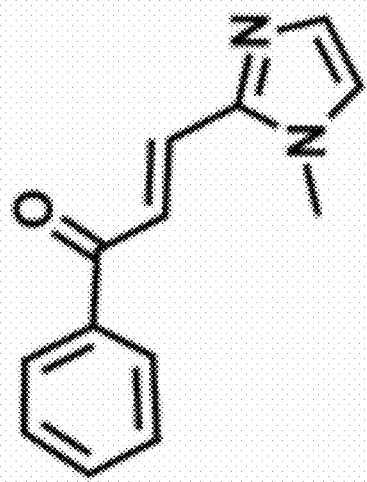
FIG. 8 shows the molecular structure of (E)-3-(1-methyl-1H-imidazol-2-yl)-1-phenylprop-2-en-1-one (ImAG std), according to an embodiment of the present invention.
Figure 9:
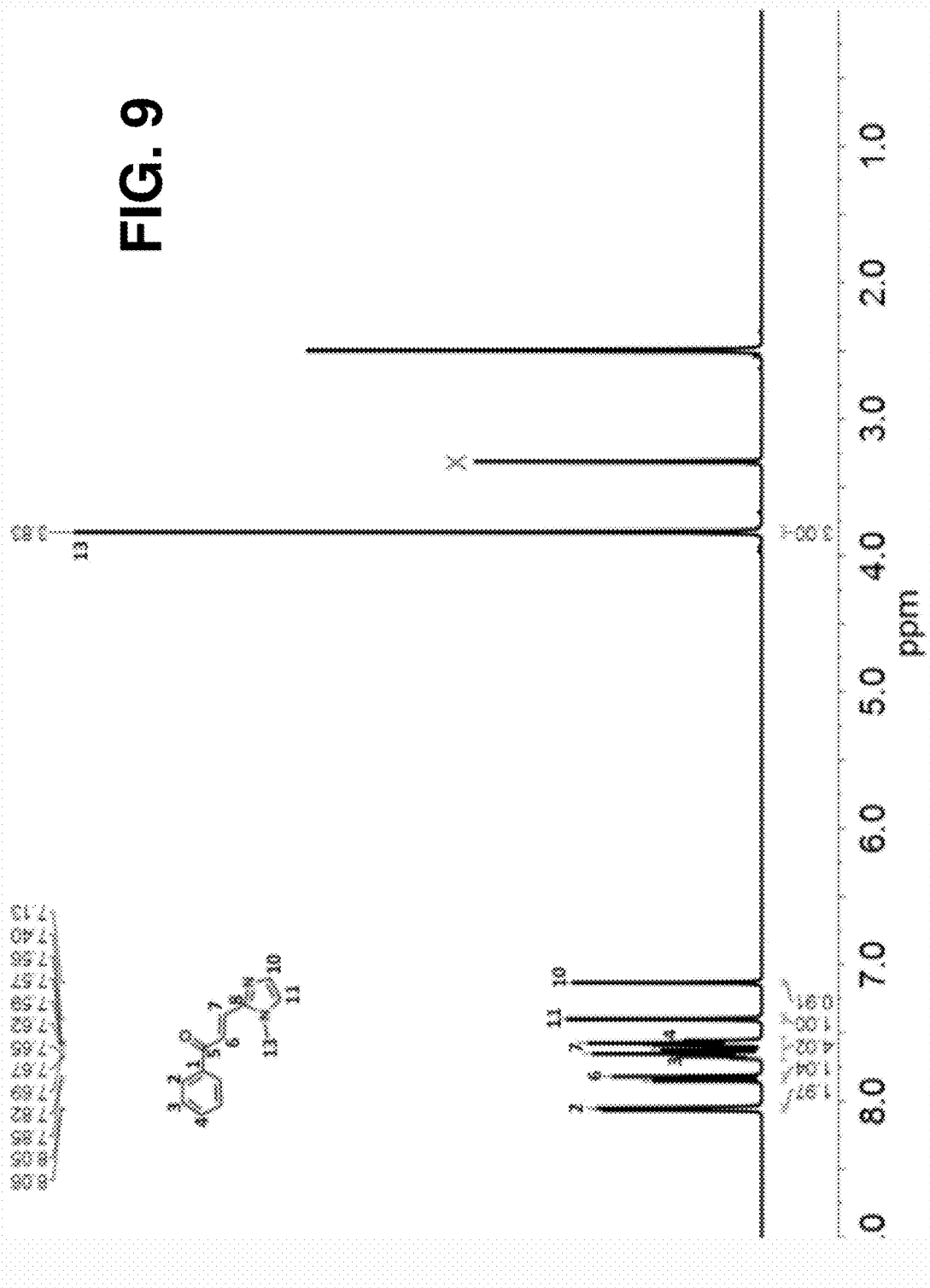
FIG. 9 shows $^1$H NMR of ImAG std, according to an embodiment of the present invention.
Figure 10:
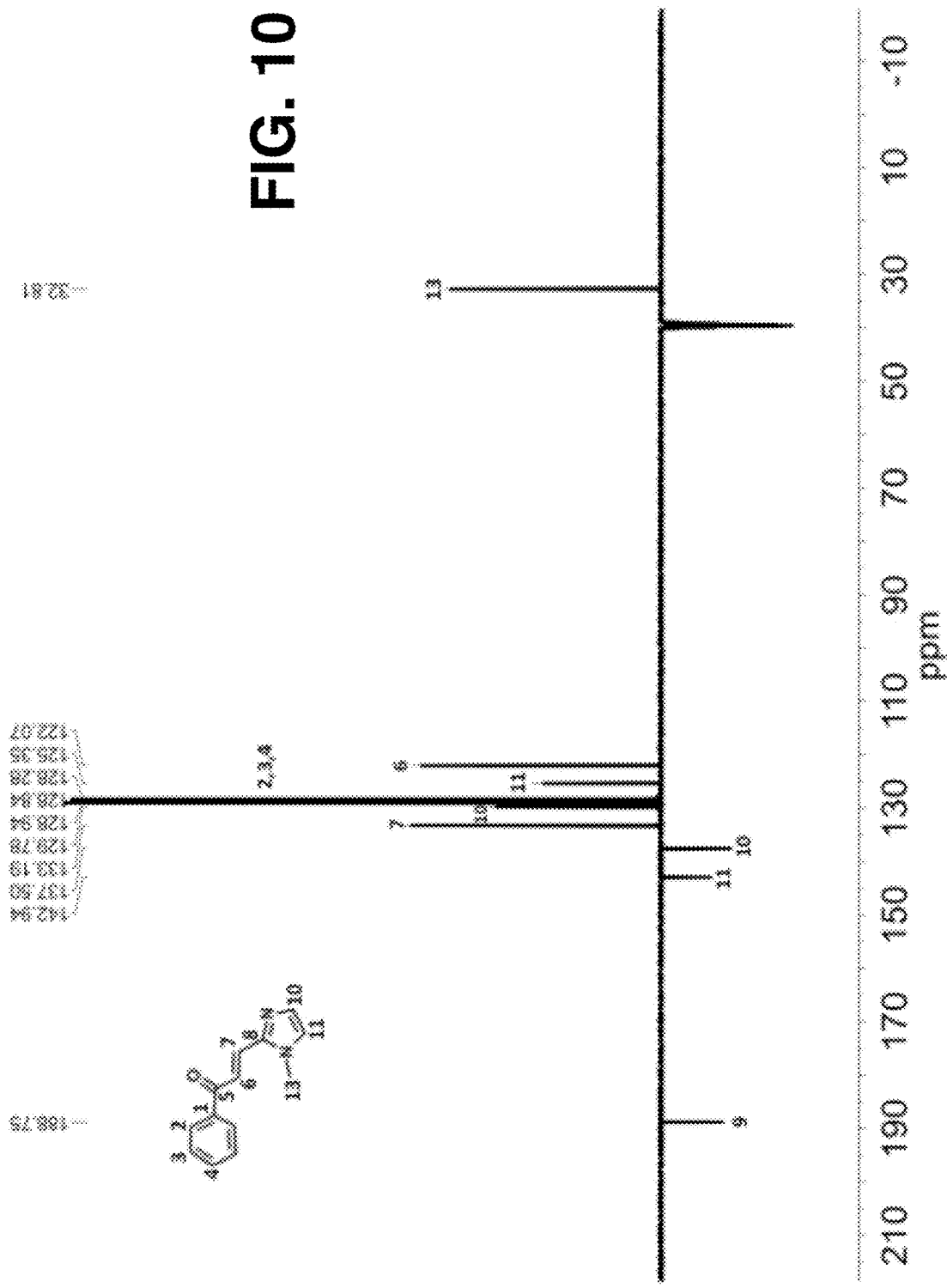
FIG. 10 shows $^{13}$C NMR of ImAG std, according to an embodiment of the present invention.

During the synthesis of derivatives ImAGhD2OH and ImAGpD2OH, an ImAG std (with a molecular structure as shown in FIG. 8) was constructed to obtain information of the pKa of the derivative by UV-VIS measurements. This allowed to study the effect of the functionality added in the 8ArG derivative. Derivative (E)-3-(1-methyl-1H-imidazol-2-yl)-1-phenylprop-2-en-1-one (ImAG std), with a chemical formula $C_{13}H_{12}N_2O$, offers an alternative method to determine the pKa without having to perform the entire synthetic sequence for the corresponding compounds ImAGhD2OH and ImAGpD2OH. In the case of ImAG standard, the same procedure as above was followed, but the obtained solid was washed with ether and hexane. ImAG std was characterized as shown in FIG. 9 and FIG. 10 by using $^{1}H$ NMR and $^{13}C$ NMR, respectively. Yellow solid, mp (125.2-126.3) ° C. TLC (100% EtOAc): $R_F=0.7$ (EtOAc); 90% yield. $^{1}H$ NMR (500 MHz, DMSO-$d_6$): δ 8.07 (d, J=7.79 Hz, 2H), 7.85 (d, J=15.10 Hz, 1H), 7.68 (t, J=6.97 Hz, 2H), 7.66 (d, J=15.17 Hz, 1H), 7.58 (t, J=7.57 Hz, 1H), 3.83 (s, 3H). $^{13}C$ NMR (126 MHz, DMSO-$d_6$): δ 188.75, 142.94, 137.50, 133.19, 129.78, 128.94, 128.84, 128.28, 125.35, 122.07, 32.81. IR ($v_{max}/cm^{-1}$) 3716.6, 3124.5, 1656.8, 1643.3, 1600.8, 1573.8, 1550.7, 1502.5, 1479.3, 1444.6, 1409.9, 1276.8, 1010.7, 767.6, 715.6. ESI-MS $[M+Na]^+$ 235.5438 m/z.

Procedure to Induce Formation of Supramolecular Structures

Figure 11:
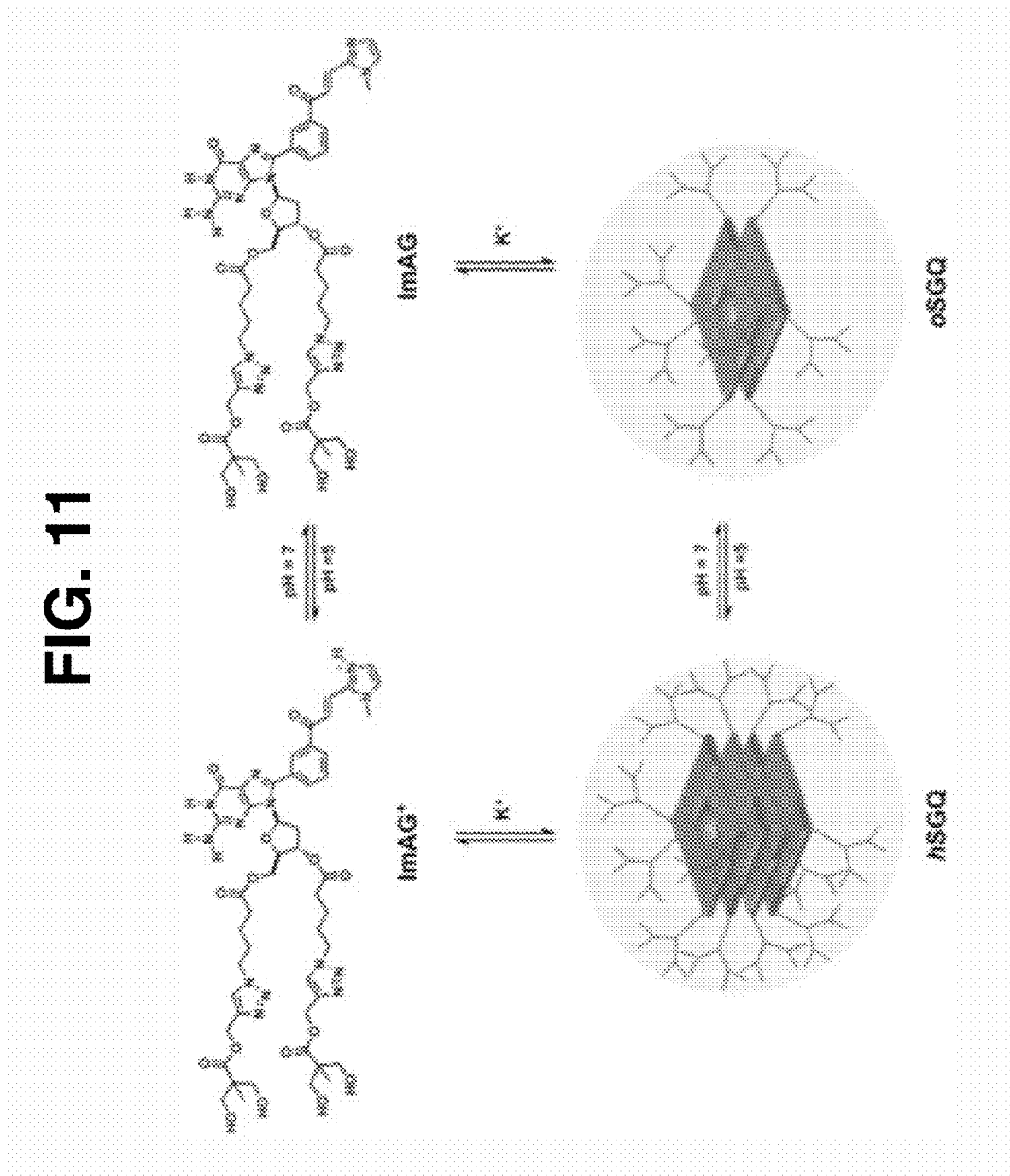
FIG. 11 shows modulation of ImAGpD2OH (ImAG) assembly in specific supramolecular structures, according to an embodiment of the present invention.

One important aspect of the invention is the self-assembly properties of the small molecule of ImAG in the presence of salt (e.g., KI) at a certain pH as seen on FIG. 2. At pH 7, in the presence of KI (2-4 M), ImAG self-assembles into precise supramolecules composed of 8 subunits that we termed octameric SGQs (oSGQ). But at pH 5 (2-4 M of KI), ImAG self-assembles into a precise SGQ composed of 16 subunits that we termed hexadecameric SGQ (hSGQ). These resulting SGQs are responsive to external stimuli such as heat and pH (e.g., changes in acidity) by forming meso-globular gel-like SHS as shown in FIG. 11.

Solution Preparation

Solutions of 0.650 mL of ImAGhD2OH were prepared at 5 mM with 4 M KI. In the case of ImAGpD2OH, the solutions prepared were 5 mM with 2 M KI. By following this procedure the following ratio is recommended between ImAGhD2OH (or ImAGpD2OH) with KI salt: 0-10 mM of ImAGhD2OH (or ImAGpD2OH) with 2-4 M KI. To dissolve the solids it was prepared a 0.1 M sodium acetate buffer for pH values of 5, 5.1, 5.2, 5.3, 5.4, 5.5, 5.6, 5.7, 5.8, 5.9. For pH 6-7, PBS from Fisher Scientific was used. The samples were put in the refrigerator (−10° C.) overnight (~12 h) for equilibration. This sample concentration was used for turbidity experiments, DSC, and DLS experiments. The concentrations of the resulting assemblies of SGQ and f-SHS were calculated in terms of the molecular weights of monomeric 8ArG derivative ImAGpD2OH or ImAGhD2OH.

Self-Assembly NMR Studies

To confirm that the self-assembly of ImAGhD2OH (or ImAGpD2OH) was successful after the solid entered in solution, the supramolecular G-quadruplex assembly (SGQ or supramolecular structure) assembly by $^{1}H$ NMR was confirmed. Self-assembly studies were carried out using a Bruker AV-500 NMR spectrometer, equipped with a 5 mm BBO probe. In water, a conventional 1D presaturation pulse sequence with the excitation pulse set over the water peak at 4.7 ppm was used. A standard proton sequence was used for experiments in $D_2O$. Self-assembly studies were performed, for example, using a 10 mM solution of ImAGhD2OH in 650 μL of $H_2O$ were 10% of standard (Sodium 3-(trimethylsilyl)propionate-2,2,3,3-$d_4$ from Aldrich) was used in $D_2O$ (9:1 $H_2O$: $D_2O$, 4 M KI, 298 K). The same conditions were used for ImAGpD2OH, but with 2 M of KI.

Figure 12:
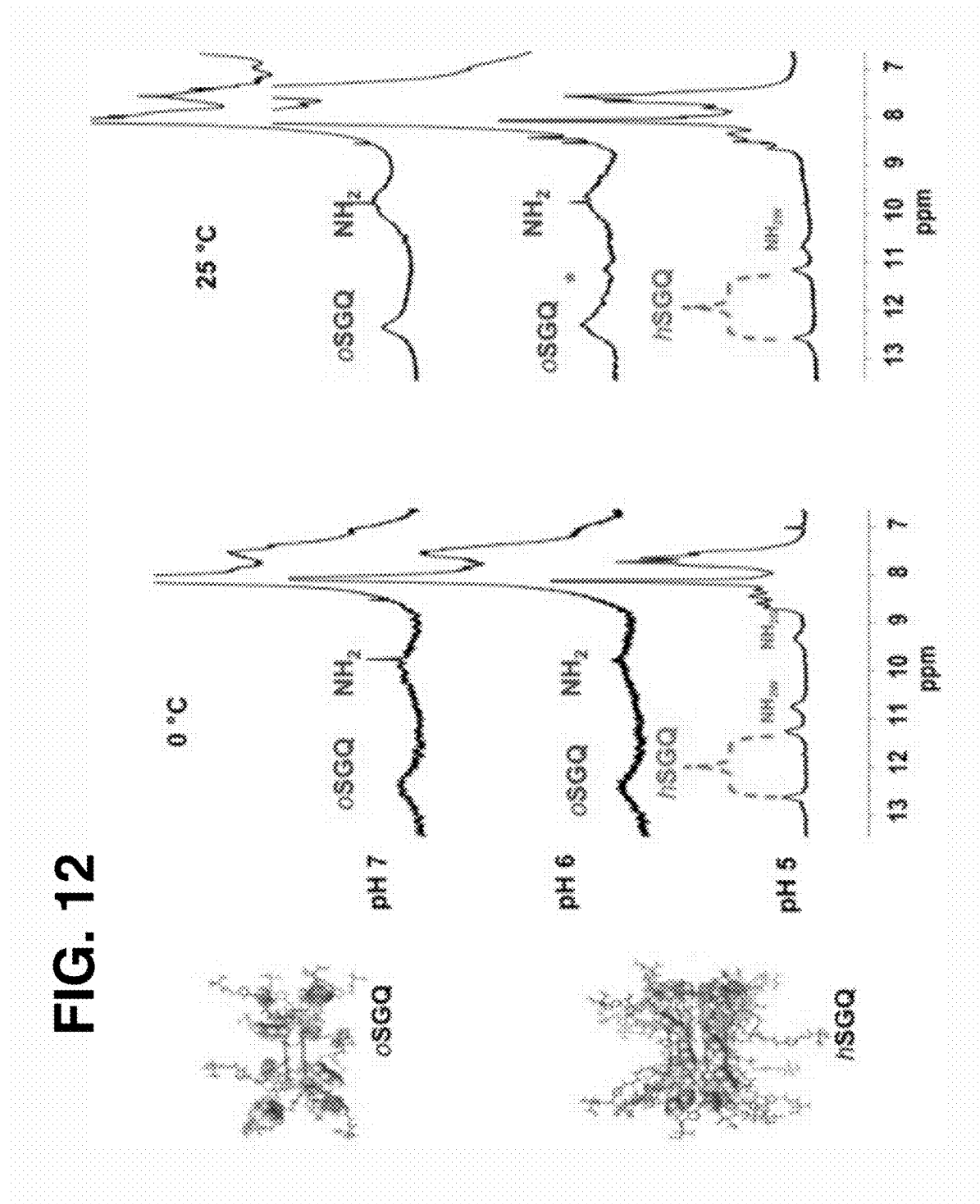
FIG. 12 shows $^1$H NMR spectra for ImAGhD2OH at 0° C. and 25° C. at pH 5, 6 and 7, according to an embodiment of the present invention.

To study the resulting assembly of compounds ImAGhD2OH and ImAGpD2OH, $^{1}H$ NMR experiments were performed to confirm the signature peaks in the $N_1H$ region that correspond to a nanoglobular SGQ (supramolecular structure) composed of eight subunits at pH 7 (oSGQ), but at pH 5 the molecularity of the SGQ is composed of sixteen subunits (hSGQ) as shown in FIG. 12 and FIG. 13, respectively. FIG. 12 shows $^{1}H$ NMR spectra for ImAGhD2OH at 0° C. (left) and 25° C. (right) at pH 5, 6 and 7 (500 MHz, 10% $D_2O$ in $H_2O$, 10 mM of ImAGhD2OH with 4 M KI). FIG. 13 shows $^{1}H$ NMR (500 MHz, 298.1 K) for ImAGpD2OH (10 mM) in $H_2O$-$D_2O$ (9:1) with 2 M KI, shows peaks that are characteristic of an hexadecameric assembly at pH 5 (below) and a octameric assembly at pH 7 (above). At pH 6, the transition of hSGQ and oSGQ can be observed at 25° C. (FIG. 12).

Figure 14:
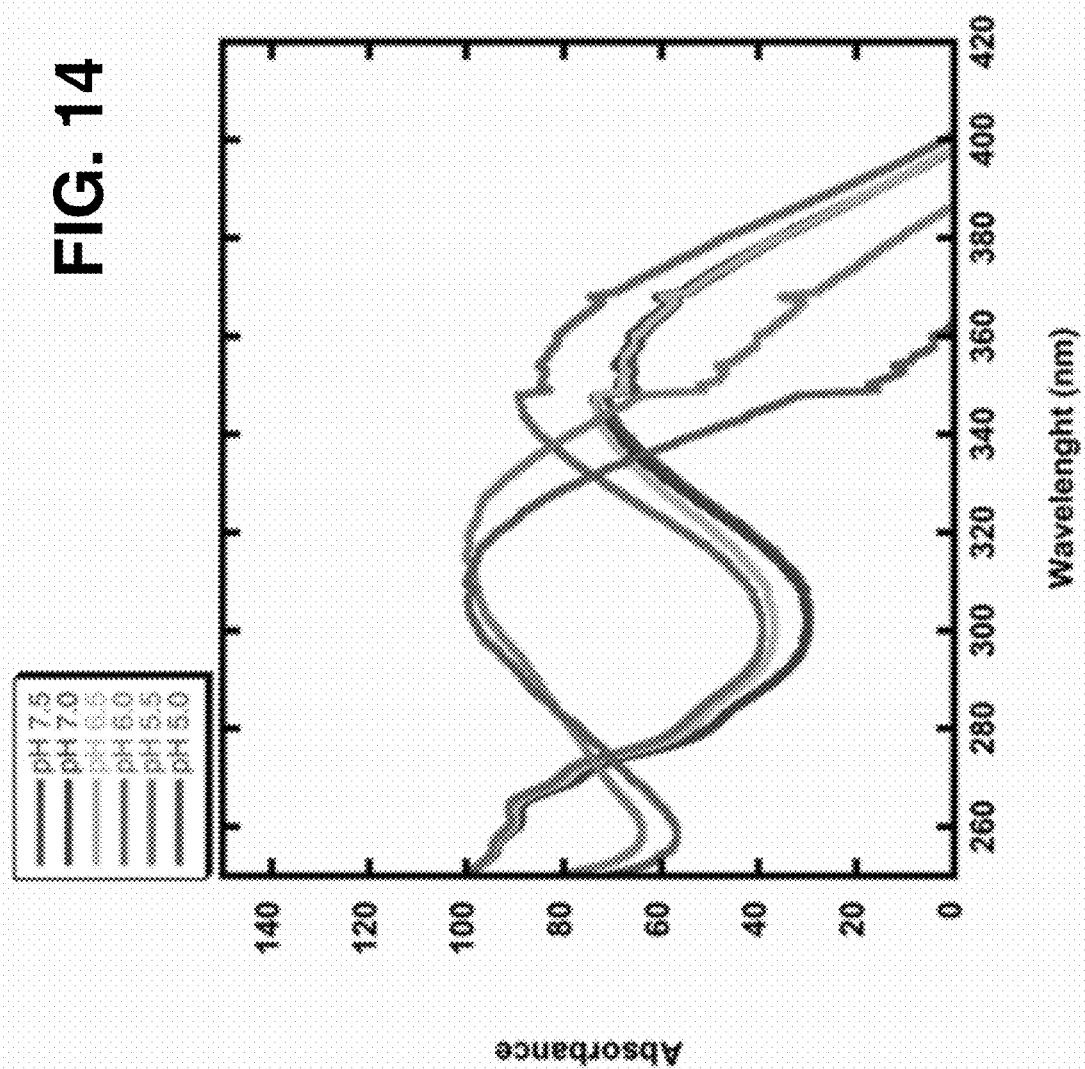
FIG. 14 shows UV absorbance of spectrum of ImAG std at pH 5, 5.5, 6, 6.5, 7 and 7.5), according to an embodiment of the present invention.

Procedure to Measure a Transition pH that Induces Formation of Cluster of Self-Arranged Supramolecular Structures Before the imidazole modification of ImAGpD2OH and ImAGhD2OH, chalcone imidazole standard derivative (E)-3-(1-methyl-1H-imidazol-2-yl)-1-phenylprop-2-en-1-one (ImAG std) was synthesized by the same aldol condensation method to obtain an estimation of the pKa by measuring the absorbance at different pHs in a Varian UV-visible spectrometer, Model Cary Bio-100 as shown in FIG. 14. For the transition pH measurement, Isothermal measurements at 26.0° C. were performed in a SPECTRAmax 340 microplate reader at 650 nm. In these experiments 100 µL of sample was added in each well in triplicate for pH: 5, 5.1, 5.2, 5.3, 5.4, 5.5, 5.6, 5.7, 5.8, 5.9, 6.0, 6.5, 7.0 and 7.5. After the microplate wells were filled, the microplate was placed in the refrigerator (−10° C.) for equilibration. Afterwards, an 85% weighted curve fit was performed to the obtained graph. According to the standard experiments performed, the pKa of ImAG std is between 5.5 and 6.

Figure 15:
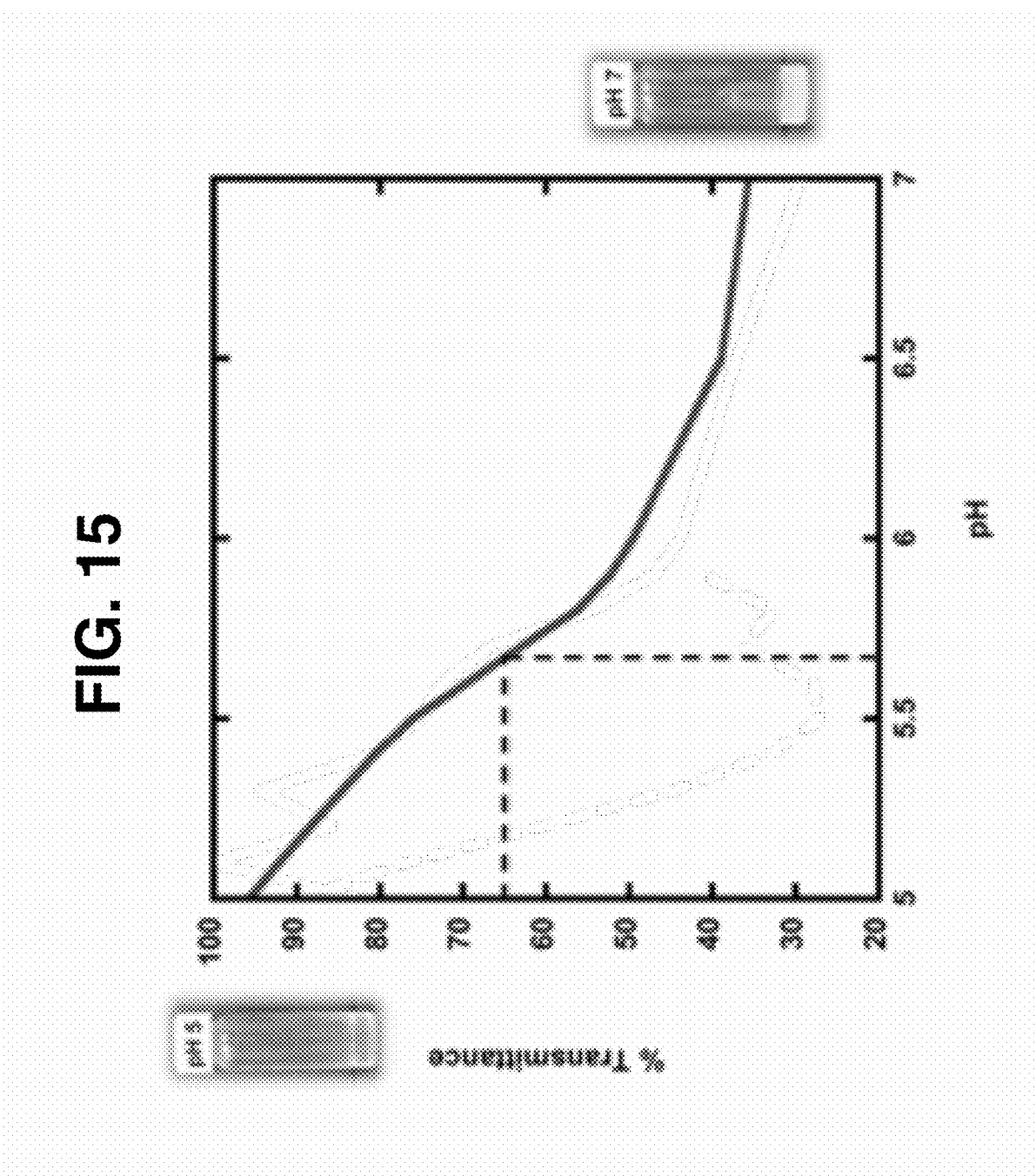
FIG. 15 shows an isothermal turbidity curve for ImAGhD2OH at 26° C. and 650 nm, according to an embodiment of the present invention.

Also, isothermal turbidity experiments of ImAGhD2OH (transmittance at 650 nm, 26° C.) confirmed a pH-responsive behavior revealing a transition pH around 5.7 at 65% of the transmittance as shown in FIG. 15. Aside from the effect of the pH on the precise assembly of the nanoglobular SGQs, we observed, at 26° C., a pH-responsive phase transition where, at pH 5 the system is in solution, but changing it to pH 7 results in the solution becoming cloudy.

Procedure of Formation of SHS by Temperature or pH

Figure 16:
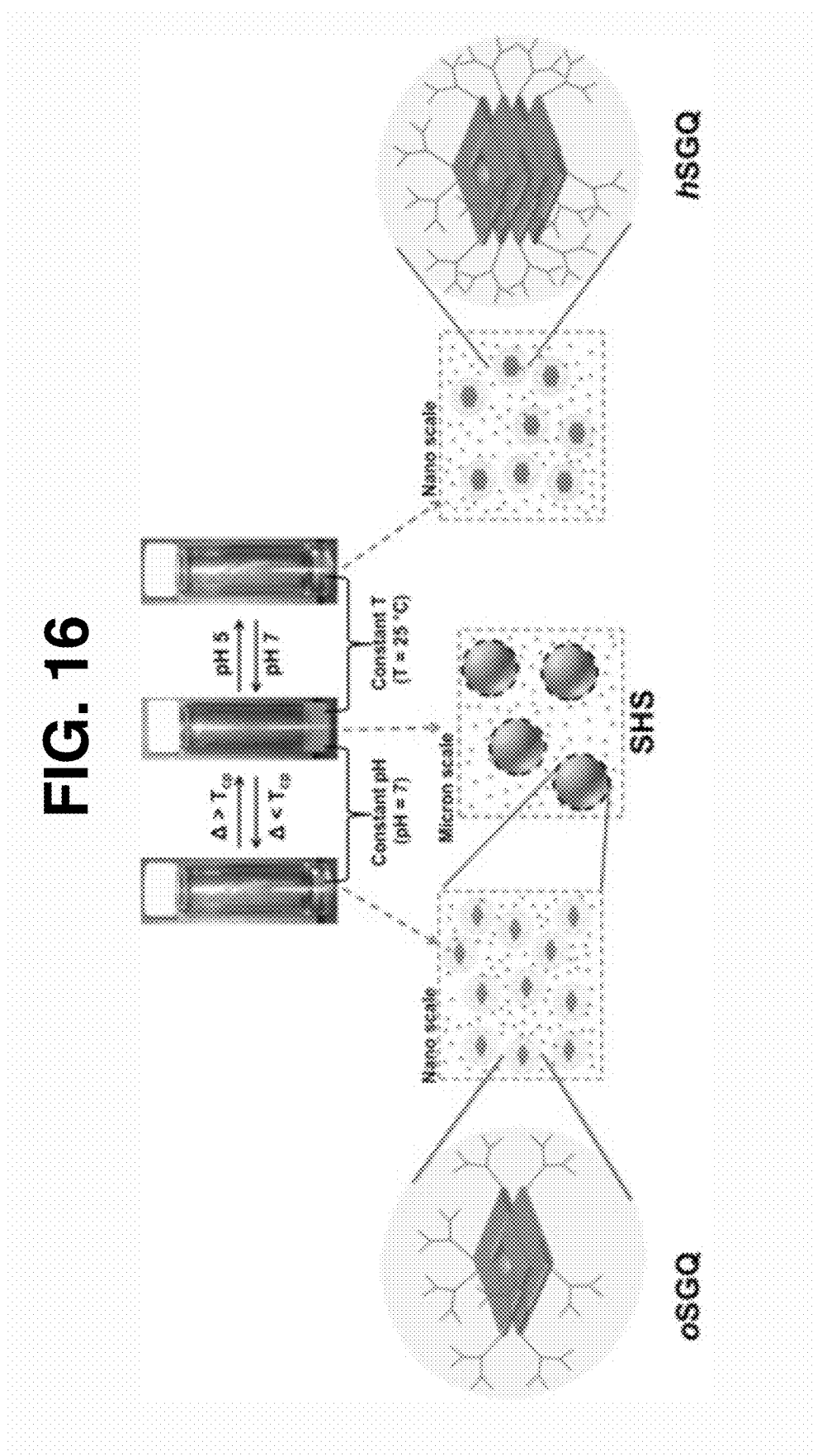
FIG. 16 illustrates the formation of Supramolecular Hacky Sacks (SHS) by different stimuli (pH or temperature), according to an embodiment of the present invention.

One aspect of the present invention is directed to a method of constructing SHS microparticles, which as previously explained, are composed of SGQs, which in turn are composed of ImAG (ImAGpD2OH or ImAGhD2OH) small molecules. The construction process of the SHS starts by the self-assembly of ImAG molecules in the presence of a suitable salt (e.g., KI) leading to the formation of SGQs that are composed of precisely eight (8) ImAG subunits (at pH 7) or sixteen (16) ImAG subunits (at pH 5). The SGQs in turn can be triggered to further self-assembly to form the SHS via heating the sample above a threshold temperature or via a change in pH (e.g., acidity of the medium) as illustrated in FIG. 16.

Procedure to Measure a Transition Temperature that Induces Formation of Cluster of Self-Arranged Supramolecular Structures Turbidimetry Studies ($T_{cp}$)

Figure 17A:
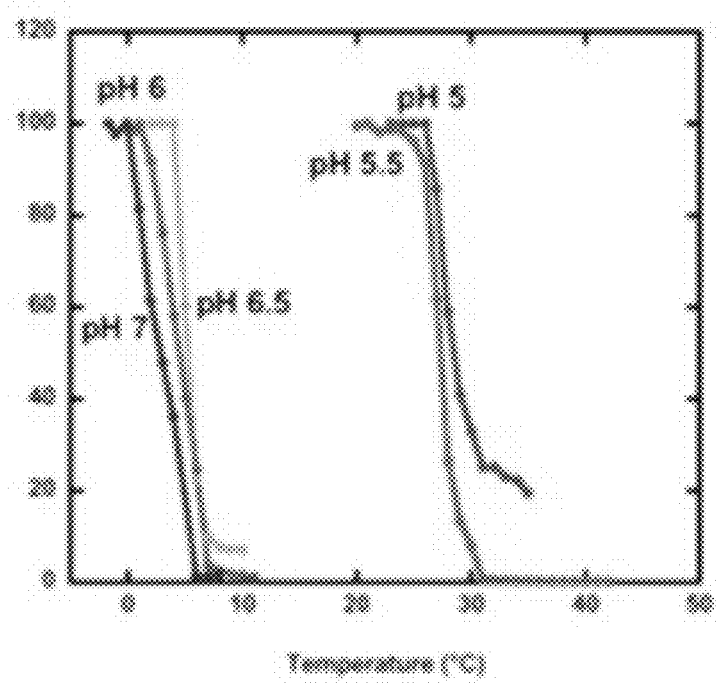
FIG. 17a shows turbidity curves measured at 650 nm for ImAGhD2OH at pH 5, 5.5, 6, 6.5 and 7, according to an embodiment of the present invention.

The effect of the imidazole moiety in ImAGhD2OH is not only limited to a pH-response behavior, the thermoresponsive behavior is maintained in the SGQ (supramolecular structure), thus exhibiting dual-responsive behavior as shown in FIG. 17a. There is a significant difference in hydrophobicity between hSGQ and oSGQ, at pHs and 5.5 the cloud-point temperature ($T_{cp}$) of protonated hSGQ is 29° C. but at pH 6-7 the $T_{cp}$ of oSGQ is around 4° C. revealing a more effective hydrophobicity in SGQ oSGQ ($\Delta T_{cp} \approx 25°$ C.). This $T_{cp}$, which is measured by turbidimetry studies in UV-Vis, is the transition temperature to form the cluster of self-arranged supramolecular structures known as supramolecular hacky sacks (SHS). The turbidity measurements were performed at 650 nm using a Varian UV-visible spectrometer, Model Cary Bio-100. The heating rate was adjusted at 2.0° C./min using Cary temperature controller apparatus from Varian.

Figure 17B:
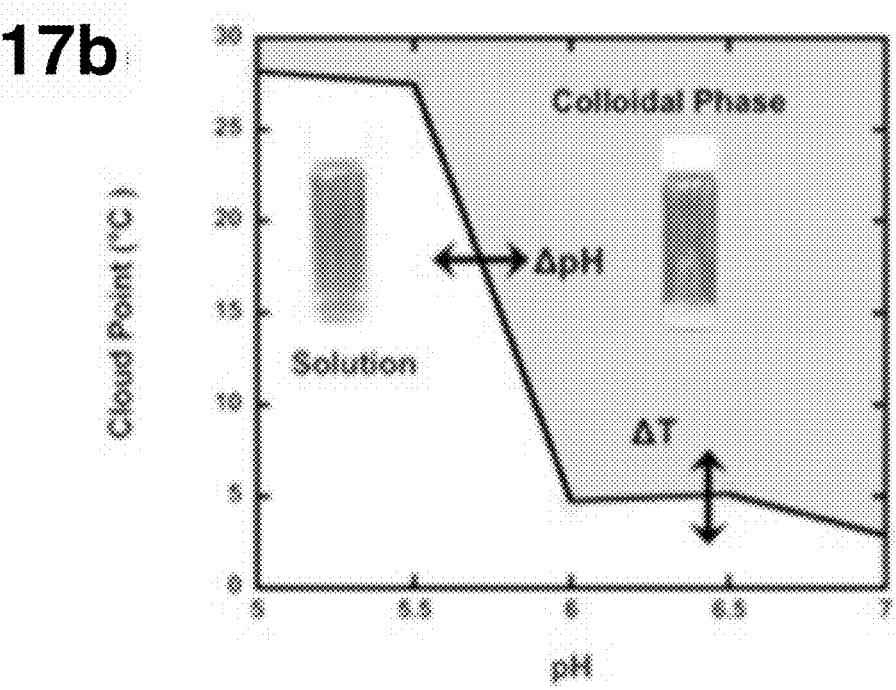
FIG. 17b shows cloud points of ImAGhD2OH from the midpoint of the change in transmittance of FIG. 17a at different pHs, according to an embodiment of the present invention.
Figure 18:
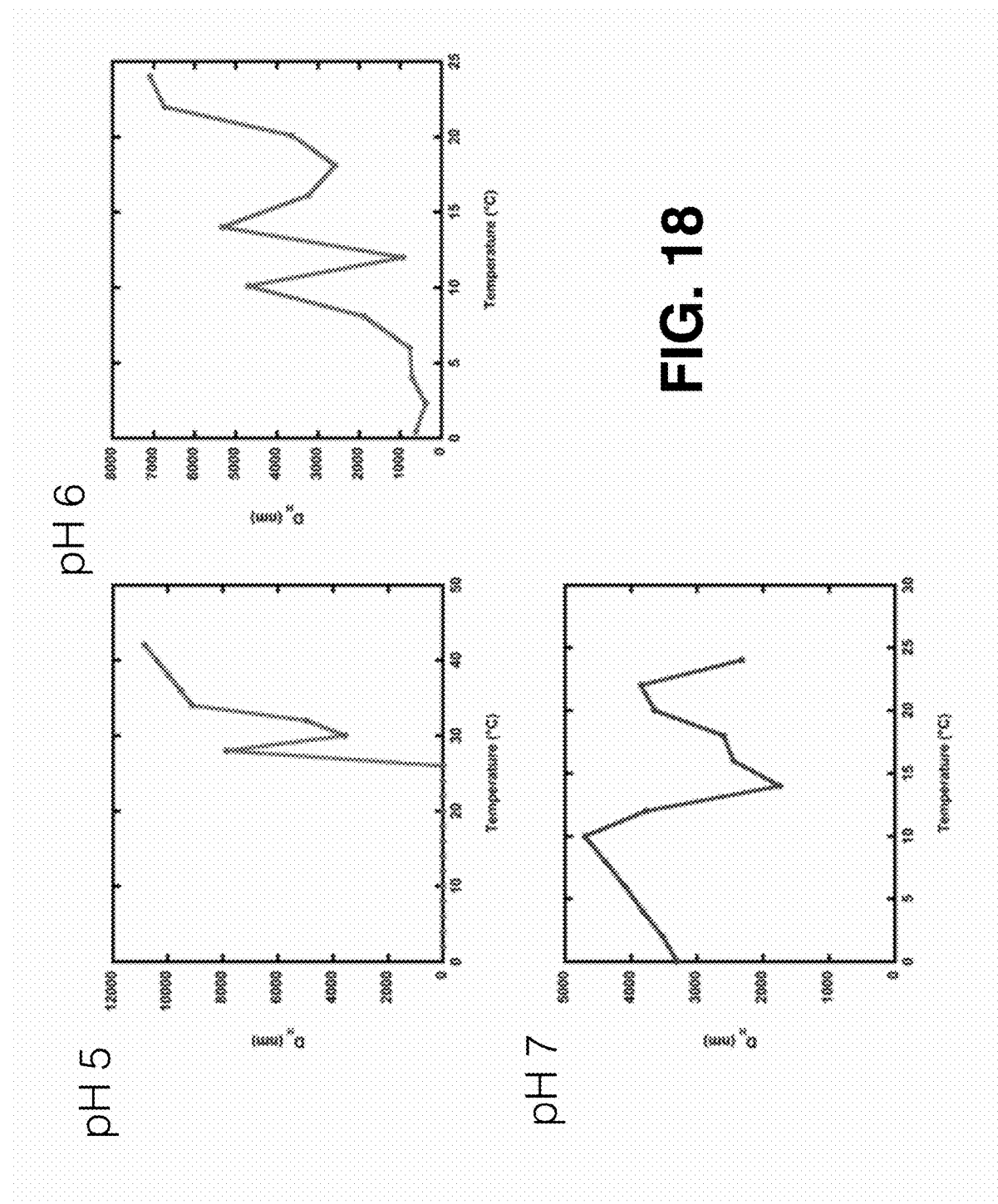
FIG. 18 shows the average hydrodynamic diameters of ImAGhD2OH as a function of temperature at pH 5, pH 6 and pH 7, according to an embodiment of the present invention.

As shown in FIG. 17b, a phase diagram was constructed to correlate $T_{cp}$ at different pH values in order to predict if hSGQs (pH<6) and oSGQ (pH>6) will be in solution or in colloidal phase transition. The phase transition region is a colloidal suspension composed of microglobules known as SHS, which were shown by dynamic light scattering (DLS) to have an average hydrodynamic diameters ($D_H$) in the range between (1.7-4.6) µm for pH 7 and (3.6-10.9) µm for pH 5 as shown in FIG. 18. There is a tendency in this mesoscopic transition to increase $D_H$ of the microglobules upon decreasing the pH. Dynamic light scattering (DLS) was used to measure the hydrodynamic size of the particles as a function of temperature from 0-74° C. The measurements were made at intervals of 2° C., allowing the temperature to stabilize before each measurement. The measurements were performed with samples (5 mM) dissolved in phosphate-buffered solution at pHs 6 and 7. For pH 5, aqueous acetate-buffered solution was used. A Brookhaven Instrument BI-90 Plus Particle Size with a diode laser at 90° of scattering angle was used with a wavelength at 657 nm and a power of 15 mW. Samples were dispersed in a buffer solution of pH 5, 6 and 7 in a centrifuged in a Daigger Mini-Centrifuge model Sprout. Then 0.30 µL were tacked from the supernatant and analyzed.

b) Differential Scanning Calorimetry (DSC) Experiments ($T_t$)

Figure 19:
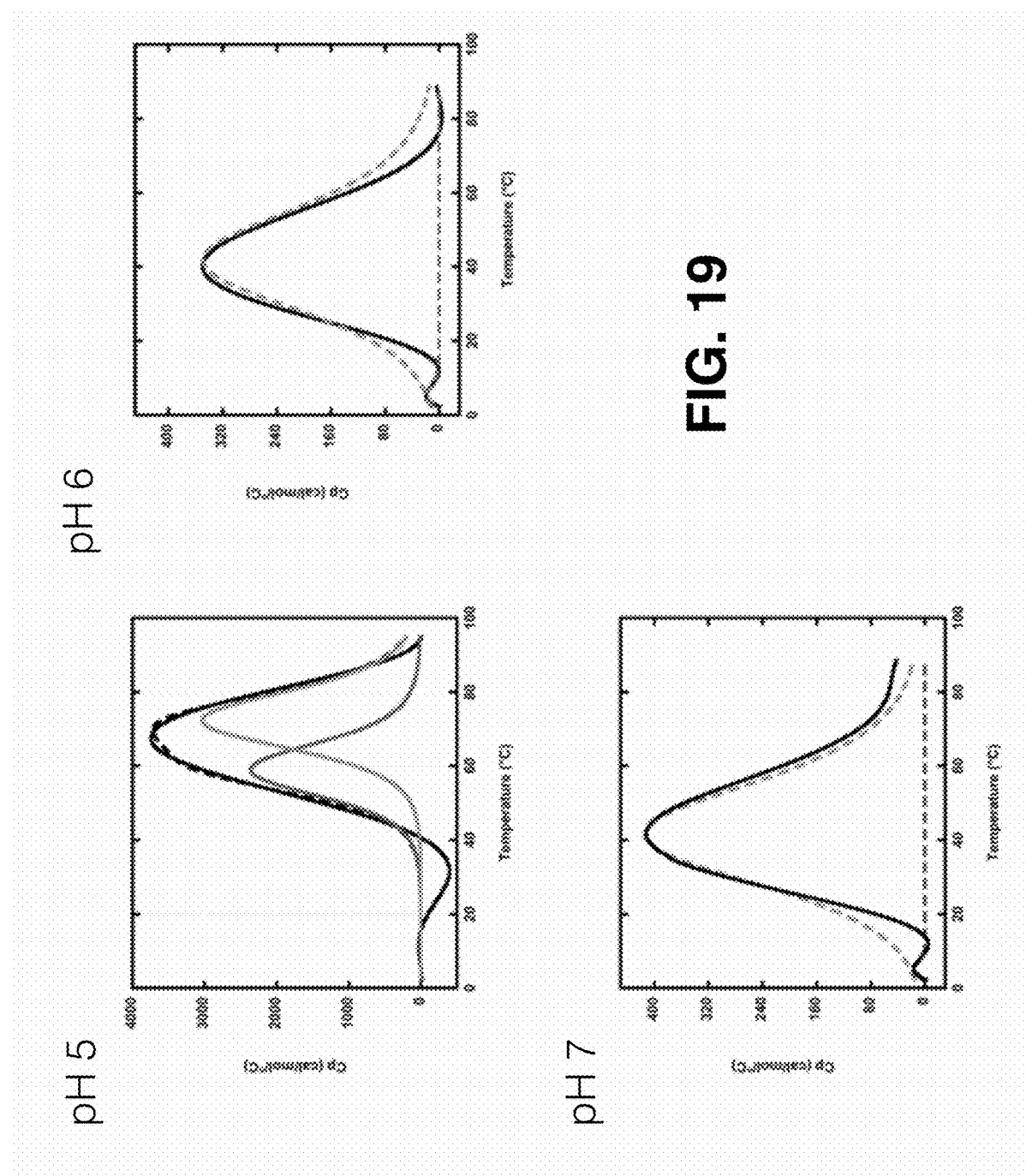
FIG. 19 shows DSC endotherm of ImAGhD2OH at pH 5.0, pH 6.0 and pH 7.0, according to an embodiment of the present invention.

These DSC experiments support the performed turbidity experiments and with additional thermodynamic parameters provide an insight into the enthalpy of the SGQs assemblies at different pHs as shown in FIG. 19, which provides DSC endotherm of ImAGhD2OH at pH 5.0, pH 6.0 and pH 7.0 with the resulting deconvolution peaks representing the ($T_t$) (curve to the left) and the ($T_m$) (curve to the right). The DSC endotherm transition reveals two processes that can be measured after deconvolution; first peak corresponds to the energy of the transition temperature ($T_t$) of the LCST process and the second peak is the melting temperature ($T_m$) of the SGQ assembly within the microglobules at higher temperatures.

The endotherms for oSGQ at pH 7 show a $T_t$ of 5.4° C., but for hSGQ at pH 5 the $T_t$ is 59.3° C. as seen in Table 1 below. Like in the turbidity experiments, there's a significant difference in $T_t$ ($\Delta T_t \approx 53.9°$ C.) between SGQs oSGQ and hSGQ that can be related to the protonation of the imidazole moiety in hSGQ at pH<6. The effect of the imidazole protonation in the SGQ (supramolecular structure) assembly is reflected in the $T_m$ of hSGQ and oSGQ, which are 72.7° C. and 42.6° C., respectively, with oSGQ being the least thermally stable assembly as shown in Table 1 below. The evident discrepancy between the onset of turbidity ($T_{cp}$) and $T_t$ of the maximum DSC peak in hSGQ was observed in previous reported SGQs and micellar telechelic poly(N-isopropylacrylamide) (PNIPAM) reported by Winnik and co-workers. This phenomenon is related to an athermal association process between the nanoglobular SGQ assemblies by non-covalent interactions of the hydroxyl groups of the periphery with the water molecules. The water-mediated association process is reflected in the SHS microglobules with sizes large enough to scatter light during the phase transition (measured by the $T_{cp}$). However, the separation of water molecules of hydration shell of the SGQ to the bulk is below the detection of the calorimeter resulting in higher $T_t$ values that are related to the energy required to expel associated water molecules. The enthalpy ($\Delta H_t$) of this phase transition process is related to the number of water molecules associated with the hydration shell of the SGQ microglobules. This is presented in the low amount of water molecules associated in oSGQ at pH 7 with a $\Delta H_t$ of 0.078 kcal/mol in comparison with the high magnitude value ($\Delta H_t$) in hSGQ at pH 5. Interestingly, at pH 5.5 (near the transition pH 5.7), there is a significant change in the magnitude of $\Delta H_t$ to 146 kcal/mol showing the effect of the number of water molecules associated during the assembly process between oSGQ and hSGQ.

Table 1 shows the thermodynamic parameters for the LCST phenomenon ($T_t$) and for the melting of ImAGhD2OH at different pH values in aqueous solution as determined by DSC. The $\Delta G_{cal}$ and $\Delta S_{cal}$ values shown in this table correspond to those calculated using the values of $T_t$, $T_m$, and $\Delta H_{cal}$ from the instrument. All $\Delta G$ values were calculated at a temperature of 20° C.

TABLE 1

| pH | $T_t$ (° C.) | $\Delta G_{Tt}$ (kcal/mol) | $\Delta H_{Tt}$ (kcal/mol) | $\Delta S_{Tt}$ (kcal/mol · ° C.) | $T_m$ (° C.) | $\Delta G_{Tm}$ (kcal/mol) | $\Delta H_{Tm}$ (kcal/mol) | $\Delta S_{Tm}$ (kcal/mol · ° C.) |
|---|---|---|---|---|---|---|---|---|
| 5.0 | 59.26 | 30.67 | 46.13 | 0.778 | 72.72 | 46.64 | 64.32 | 0.884 |
| 5.5 | 54.00 | 91.92 | 146.0 | 2.704 | 68.64 | 44.34 | 62.58 | 0.912 |
| 6.0 | 5.702 | −0.309 | 0.123 | 0.0216 | 41.12 | 5.76 | 11.20 | 0.272 |
| 6.5 | 4.938 | −0.160 | 0.0522 | 0.0106 | 37.32 | 5.48 | 11.80 | 0.316 |
| 7.0 | 5.449 | −0.210 | 0.0784 | 0.0144 | 42.64 | 8.18 | 15.42 | 0.362 |

Differential Scanning calorimetry (DSC) analyses were performed on a VP-DSC Micro-Calorimeter from MicroCal and Origin (v.7) was used for data processing. For the experiment, the buffer was first degasified and the experiment was carried out as a blank in both sample and reference cell. Then, the sample was degasified, and the blank buffer in the sample cell to be substituted with sample was removed. Afterwards, the experiment was performed with a temperature ramp of 0° C.-80° C. for 4 cycles.

LCST Modulation in pH-Responsive SGQ

Figure 20:
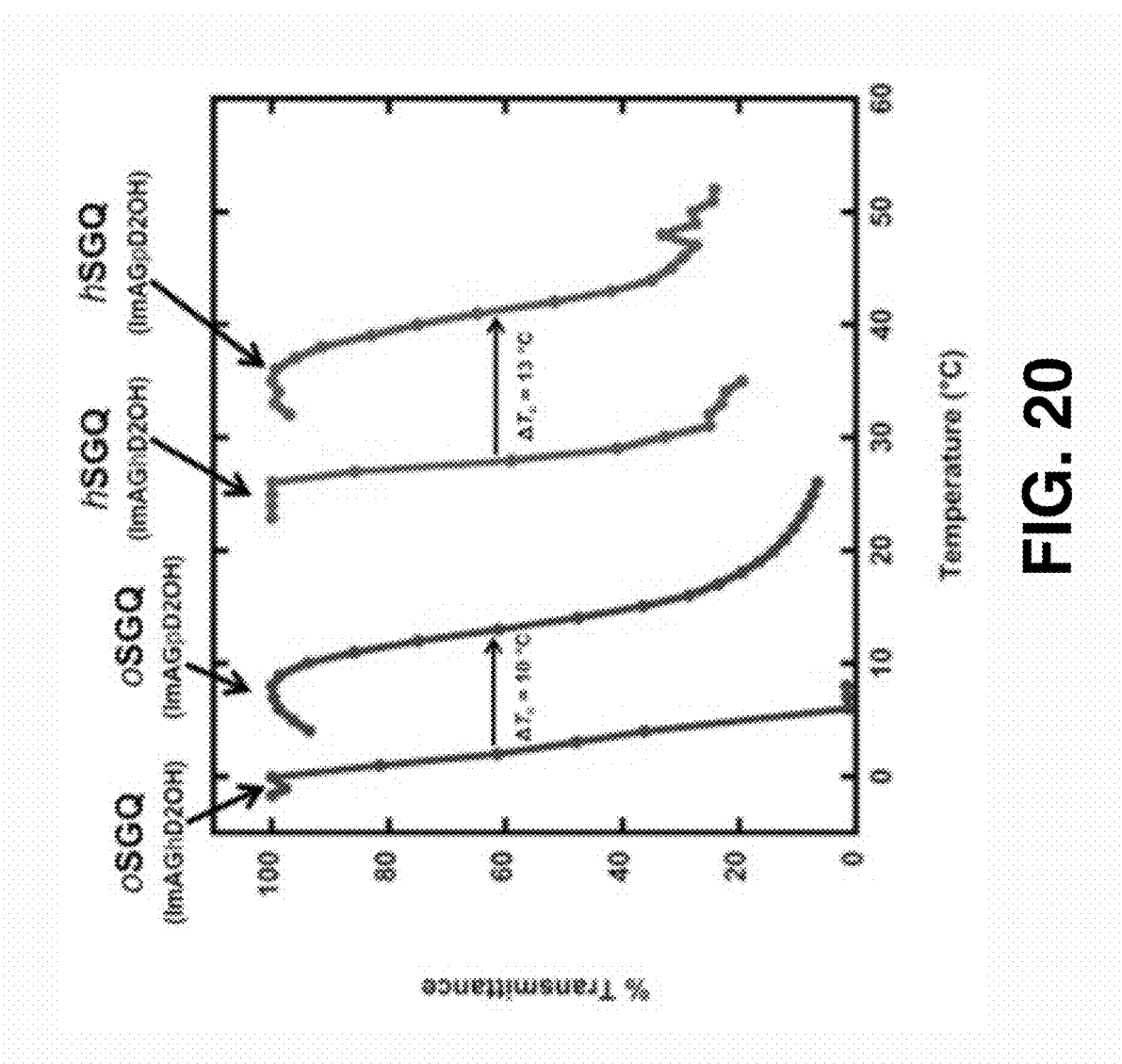
FIG. 20 shows turbidity curves for SGQs formed from ImAGpD2OH at pH 7 and pH 5, according to an embodiment of the present invention.

The present invention provides a pH and thermo responsive SGQ that can form a precise assembly hSGQ when pH<6 and oSGQ when pH>6 by the incorporation of the imidazole group in the C8 position of the guanine. But, it is know from previous reported SGQ derivatives that modulation of LCST could be achieved by changing the three-dimensional distribution of hydrophobic patches in the form of methylenes in the periphery of the ribose chains of the SGQ. For that reason, ImAGpD2OH was synthesized, which exhibits the same self-assembly properties presented in ImAGhD2OH by forming oSGQ at pH 7 and hSGQ at pH 5 as shown in FIG. 13. The effect of this hydrophobic modulation in SGQ of ImAGpD2OH is evident in the $T_{cp}$ of 15° C. for oSGQ at pH 7 and 42° C. for hSGQ at pH 5 showing a significant shift of $\Delta T_{cp}$ 10° C. and $\Delta T_{cp}$ 13° C., respectively, as shown in FIG. 20. As with ImAGhD2OH, DSC experiments also support the turbidity experiments by showing $T_t$ values in the SGQ of ImAGpD2OH of 50.5° C. and 8.6° C. at pH 5 (hSGQ) and pH 7 (oSGQ) respectively as shown in Table 2 below, which indicates thermodynamic parameters for the LCST phenomenon ($T_t$) and for the melting of ImAGpD2OH at different pH values in aqueous solution as determined by DSC. The $\Delta G_{cal}$ and $\Delta S_{cal}$ values provided in this table correspond to those calculated using the values of $T_t$, $T_m$ and $\Delta H_{cal}$ from the instrument. All $\Delta G$ values were calculated at a temperature of 20° C.

Method to Fix Cluster of Self-Arranged Supramolecular Structures

Figure 21:
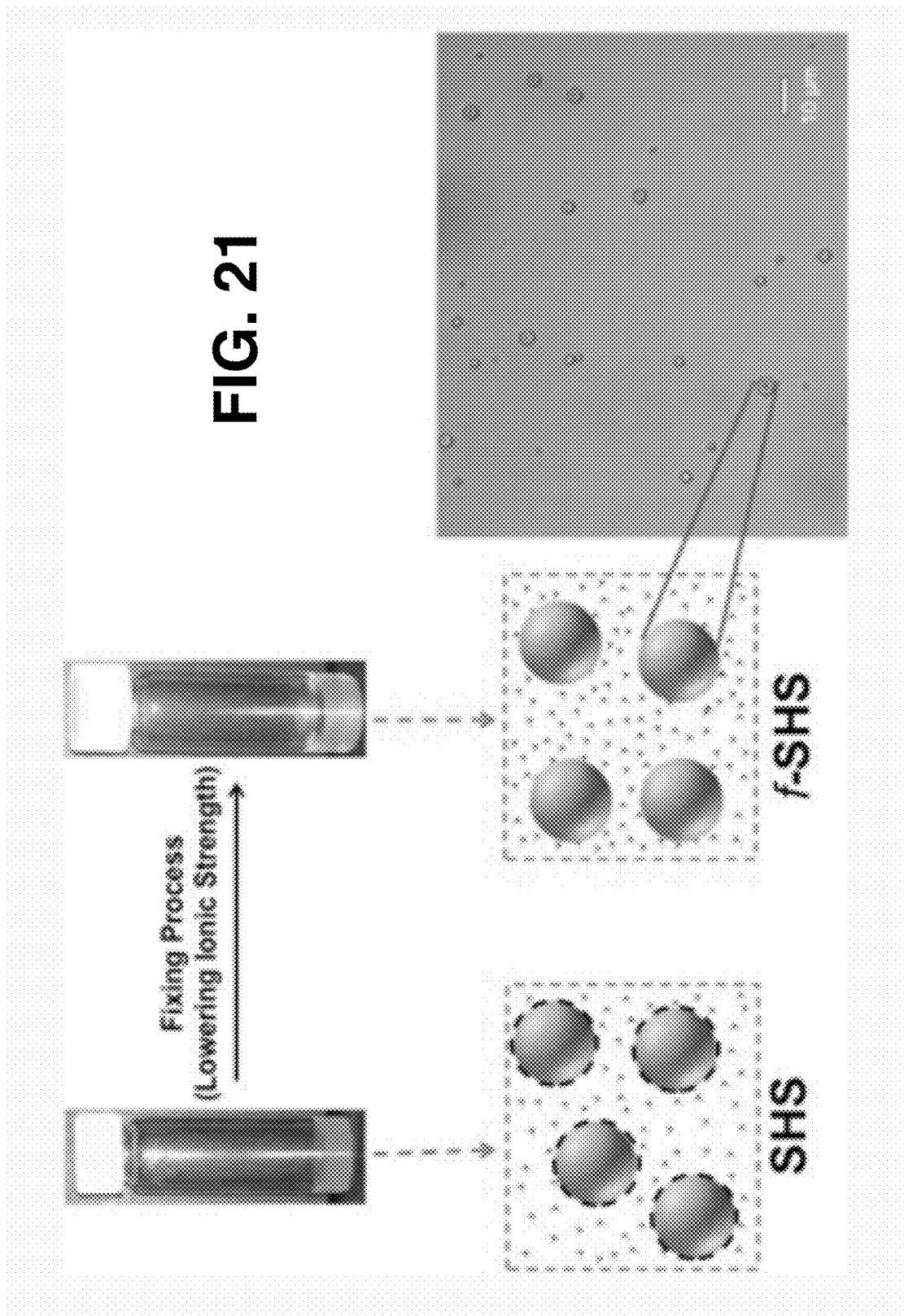
FIG. 21 illustrates the fixing process of SHS to obtain f-SHS by lowering ionic strength, according to an embodiment of the present invention.

The present invention also provides a method for stabilizing the SHS via a fixing protocol in which the resulting f-SHS (the prefix f- is added to SHS to denote a fixed SHS) tolerate a variety of physical manipulations like dilutions, pipetting, freeze-drying, transfers between different media (e.g., cell growth serum). The term "fixing" is used herein as an analogy to the process of fixing cells in cell biology (e.g., using aldehydes as cross-linking agents) to preserve its morphological features for microscopy studies. This method consists in decreasing the ionic strength of the solution from molar to millimolar range without disturbing the globular morphology of the SHS as illustrated in FIG. 21.

The fixing protocol requires no additional stabilizing substances or further covalent modifications like cross-linking agents. This protocol also serves to rinse the f-SHS after the encapsulation of a desired guest (e.g., molecules, polymers, proteins and nucleic acids) with negligible loss of such guest (as determined by evaluating the concentration of guests in the surrounding media). The rinsing of the excess guest and dilution of the f-SHS enable the use of these particles under conditions suitable for biomedical applications as described below.

The concentrations of the resulting assemblies of SGQ and f-SHS were calculated in terms of the molecular weights of monomeric 8ArG derivative ImAGpD2OH (or ImAGhD2OH). For the purpose of the following explanations, the specification will refer to ImAGpD2OH, but the same procedures apply to ImAGhD2OH. For the fixed SHS (f-SHS) concentrations, 0.1 mL of the SHS colloid was diluted at 40° C. formed by LCST in 1.57 mL of PBS (1× at pH 7.4) to obtain a resulting concentration of 0.303 mM f-SHS and 121 mM KI. By lowering the ionic strength with this dilution process, kinetically stable versions of the SHS were isolated. In other words, by using this method, f-SHS were obtained. One important advantage of this fixing process is that the f-SHS can be diluted from molar to millimolar range while preserving their integrity and shape without the need of covalent crosslinking agents or further modifications to increase the stability.

The fixing process according to the present invention will be explained in detail. The vial with the "SHS" is removed from the fridge (−10° C.-0° C.) and transferred to ice. If the sample is frozen, the sample is agitated until the ice get

TABLE 2

| pH | $T_t$ (° C.) | $\Delta G_{Tt}$ (kcal/mol) | $\Delta H_{Tt}$ (kcal/mol) | $\Delta S_{Tt}$ (kcal/mol · ° C.) | $T_m$ (° C.) | $\Delta G_{Tm}$ (kcal/mol) | $\Delta H_{Tm}$ (kcal/mol) | $\Delta S_{Tm}$ (kcal/mol · ° C.) |
|---|---|---|---|---|---|---|---|---|
| 5.0 | 50.45 | 5.07 | 8.41 | 0.167 | 70.52 | 40.85 | 57.01 | 0.808 |
| 7.0 | 8.631 | −5.74 | 4.36 | 0.505 | 56.11 | 65.20 | 101.3 | 1.805 | melted and then transferred into ice. Afterwards, the vial with the "SHS" is removed from the ice and placed in a water bath at 40° C. (temperature used have to be equal or above the $T_{cp}$ (or $T_t$) of the SGQ in solution) for about 1 min under manual stirring until the solution becomes cloudy (SHS colloid). With a micropipette, 250 µL is taken from the "SHS" vial and transferred into a first vial that already contains 750 µL of PBS (total volume 1.00 mL). The first vial is gently agitated for 1 minute to homogenize the solution. Finally, the "SHS" vial is returned immediately to the ice and the sample can be returned to the fridge.

If other concentrations of f-SHS want to be used, the following dilutions can be used. With a micropipette, 80 µL is taken from the first vial and transferred into a second vial that contains 120 µL of PBS (total volume of 200 µL).

The second vial is gently agitated for 1 minute to homogenize the solution. This process is also carried out for the other samples. With a micropipette, 32 µL is taken from the first vial and transferred into a third vial, which contains 168 µL of PBS (total volume of 200 µL). The third vial is gently agitated for 1 minute to homogenize the solution. With a micropipette, 16 µL is taken from the first vial and transferred into a fourth vial, which contains 184 µL of PBS (total volume of 200 µL). The fourth vial is gently agitated for 1 minute to homogenize the solution. With a micropipette, 4 µL is taken from the first vial and transferred into a fifth vial, which contains 196 µL of PBS (total volume of 200 µL). The fifth vial is gently agitated for 1 minute to homogenize the solution. With a micropipette, 1.2 µL is taken from the first vial and transferred into a sixth vial, which contains 298.8 µL of PBS (total volume of 300 µL). The sixth vial is gently agitated for 1 minute to homogenize the solution.

Figure 22:
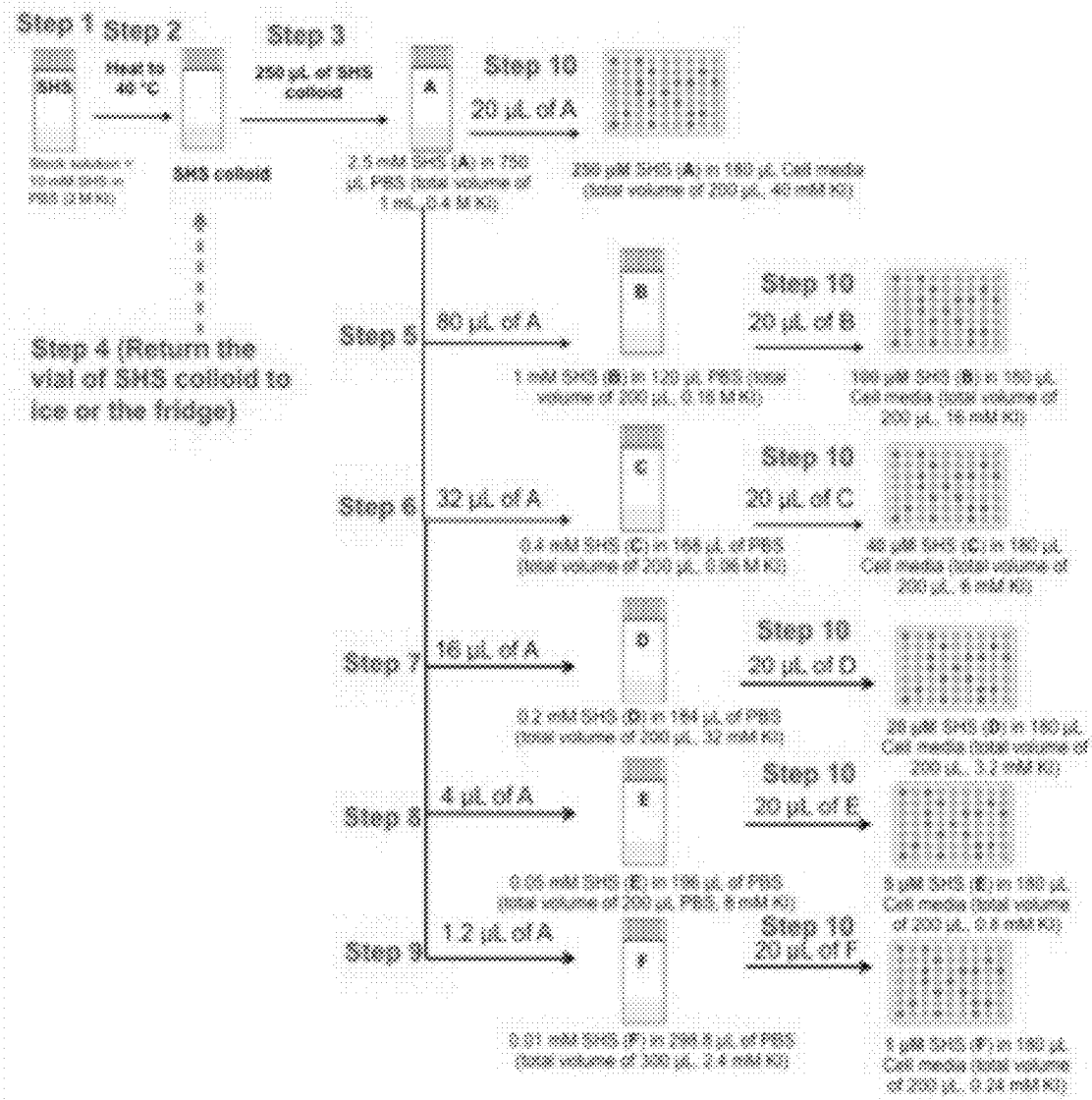
FIG. 22 shows the summary of SHS dilution preparation, according to an embodiment of the present invention.

Once the six solutions are prepared ($1^{th}$ to $6^{th}$ vials), 20 µL of each sample is transferred into 180 µL of cells in a 96-well plate (total volume of 200 µL). Each sample is measured in triplicate. The final concentrations of the first, second, third, fourth, fifth and sixth samples will be 250 µM, 100 µM, 40 µM, 20 µM, 5 µM and 1 µM, respectively. FIG. 22 illustrates the steps previously described.

Procedure for the Encapsulation Process

Figure 23:
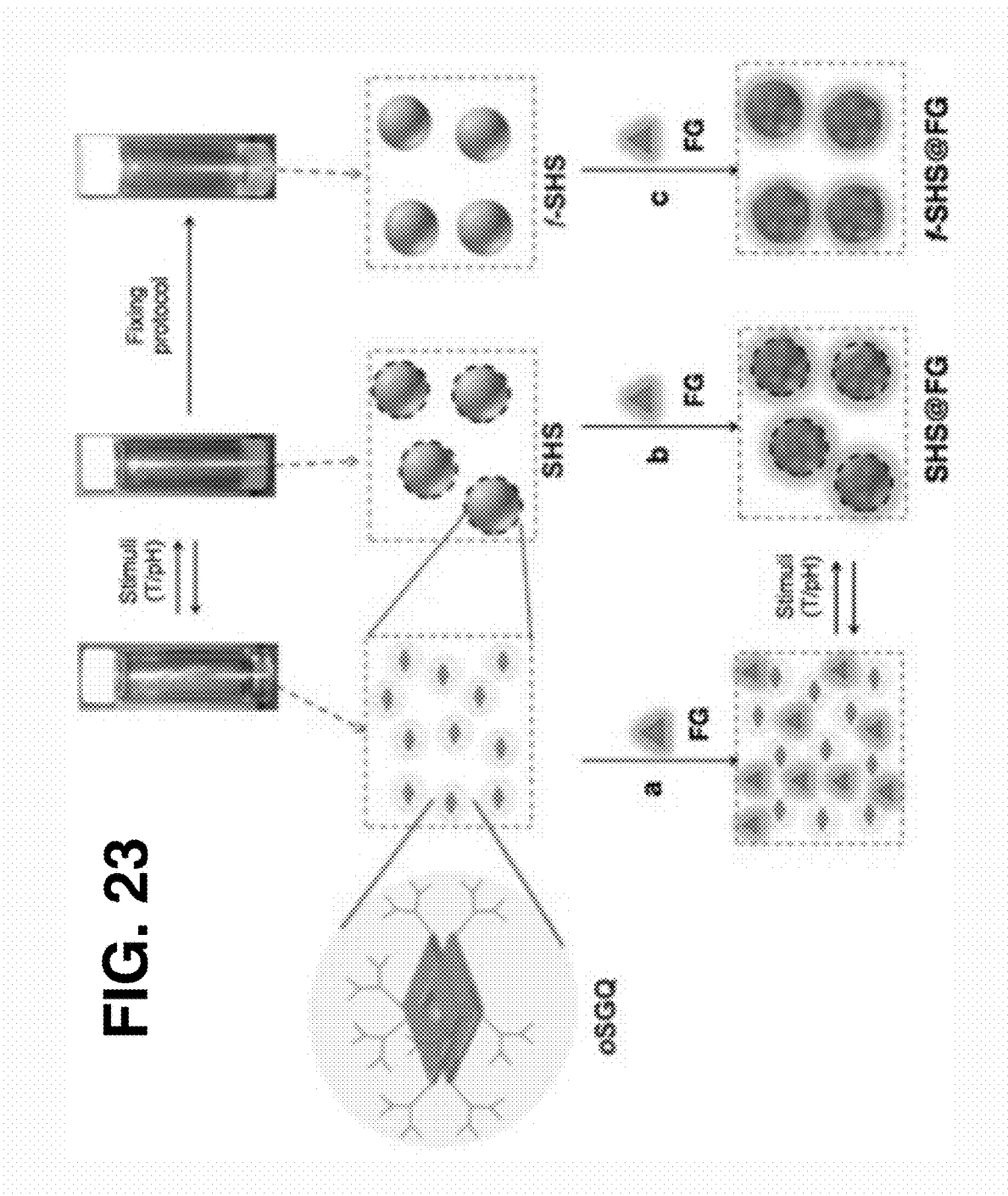
FIG. 23 illustrates the protocols of encapsulation of fluorescent guests into SHS, according to an embodiment of the present invention.
Figure 24:
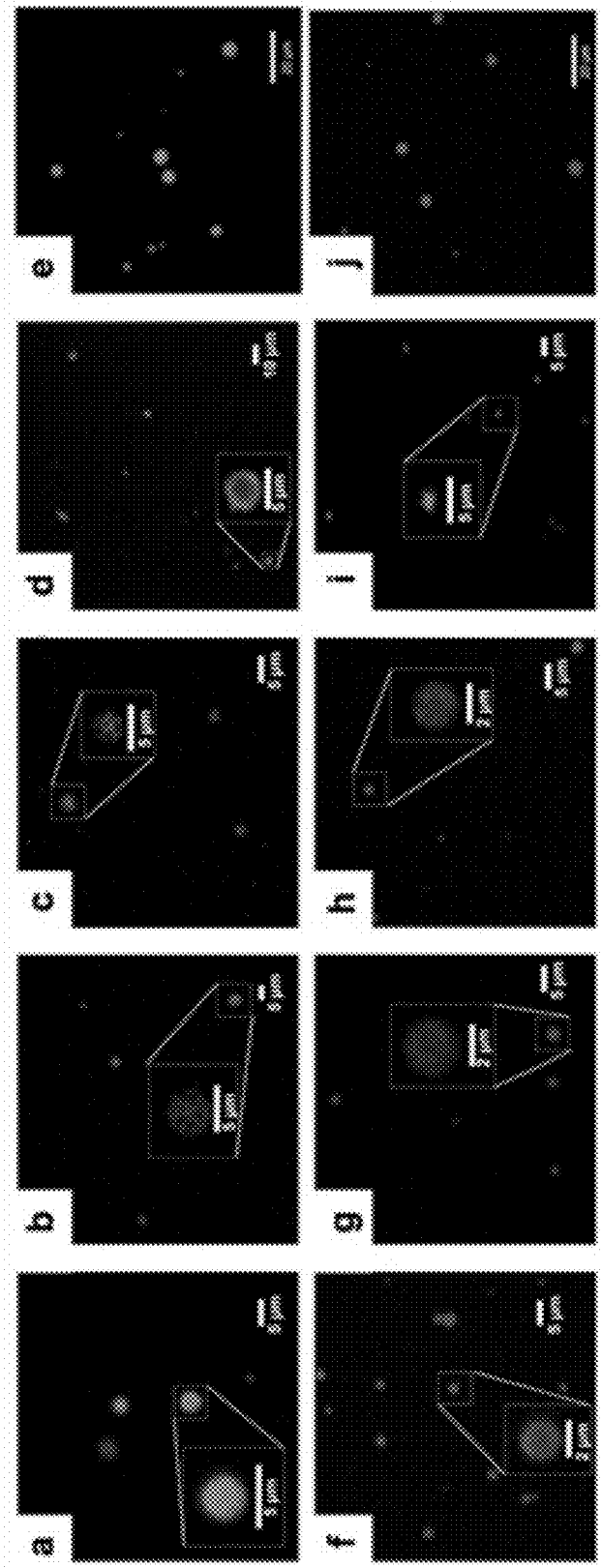
FIG. 24 shows Confocal Laser Scanning Microscopy (CLSM) microscopy images of the f-SHS encapsulating a wide variety of FG molecules via the osmotic gradient method, according to an embodiment of the present invention.

One important aspect of the invention is the capacity of the SHS and f-SHS to encapsulate a wide variety of guest molecules (e.g., drugs, proteins, DNA) due to its surface and internal porosity. Thus, the present invention provides three encapsulation protocols as illustrated in FIG. 23, which are: (i) the in situ method where the formation of the SHS is triggered in the presence of a desired guest; and the osmotic gradient methods (ii) and (iii) where a guest is incubated with a previously made SHS or f-SHS, respectively. These methods provide the flexibility to encapsulate a wide variety of guest molecules (FG), and the method of choice will depend on the specific physicochemical properties of the guest of interest. For example, small molecules that are insensitive to high ionic strengths or relatively high temperatures (e.g., doxorubicin (DOX), Rhodamine B) could be encapsulated by any of the three methods. However, methods (iii) and (ii) have the advantage of enabling the loading of higher concentration of guest, however, method (iii) is the most suitable for the encapsulation of sensitive guests like proteins that could be denatured at high temperatures and high ionic strengths. FIG. 24 shows representative confocal laser scanning microscopy (CLSM) images of the f-SHS encapsulating various different fluorescent guest molecules via the osmotic gradient method to form f-SHS@FG complexes. FIG. 24 shows small molecules: (a) Rhodamine B dye, (b) Dox anticancer drug; Proteins: (c) cytochrome C, (d) DsRed2, (i) mCherry; Polysaccharides (dextrans labeled with Texas Red) of different sizes: (f) 3 kDa, (g) 10 kDa, (h) 70 kDa; DNA oligonucleotides: (e) Fds26T; and (j) thrombin binding aptamer (TBA).

Procedure for Osmotic Gradient Method where a Guest is Incubated with a Previously Made (ii) SHS Once the SHS (5 mM of ImAGpD2OH, 2M KI) is formed at 40° C. (also a temperature equal or above the $T_{cp}$) and neutral pH, the amount of desired guest dissolved in PBS is added to the colloidal suspension. For example, to add 100 equivalents of Doxorubicin, 100 µL of Dox is added with a micropipette to the SHS colloidal suspension. The mixture is stirred for 1-3 min at 40° C., and then the fixing process procedure described before is carried out to obtain 1.65 mL of f-SHS (0.303 mM of ImAGpD2OH).

Procedure for Osmotic Gradient Method where a Guest is Incubated with a Previously Made (iii) f-SHS Once the f-SHS solution is prepared at neutral pH as previously described, 200 µL of f-SHS (0.303 mM of ImAGpD2OH) is transferred in an Eppendorf tube followed by the addition in equivalents of the guest that will be encapsulated in f-SHS. For example, for 5 equivalents of each dextran Texas Red (DTR) polymer solution 37 µL of 0.0685 mM is added to the corresponding Eppendorf tube. Then all samples are incubated for 1 h at 35° C. with movement.

Procedure for Delivery Studies

Induced pH Disassembly Guest Release

Figure 25:
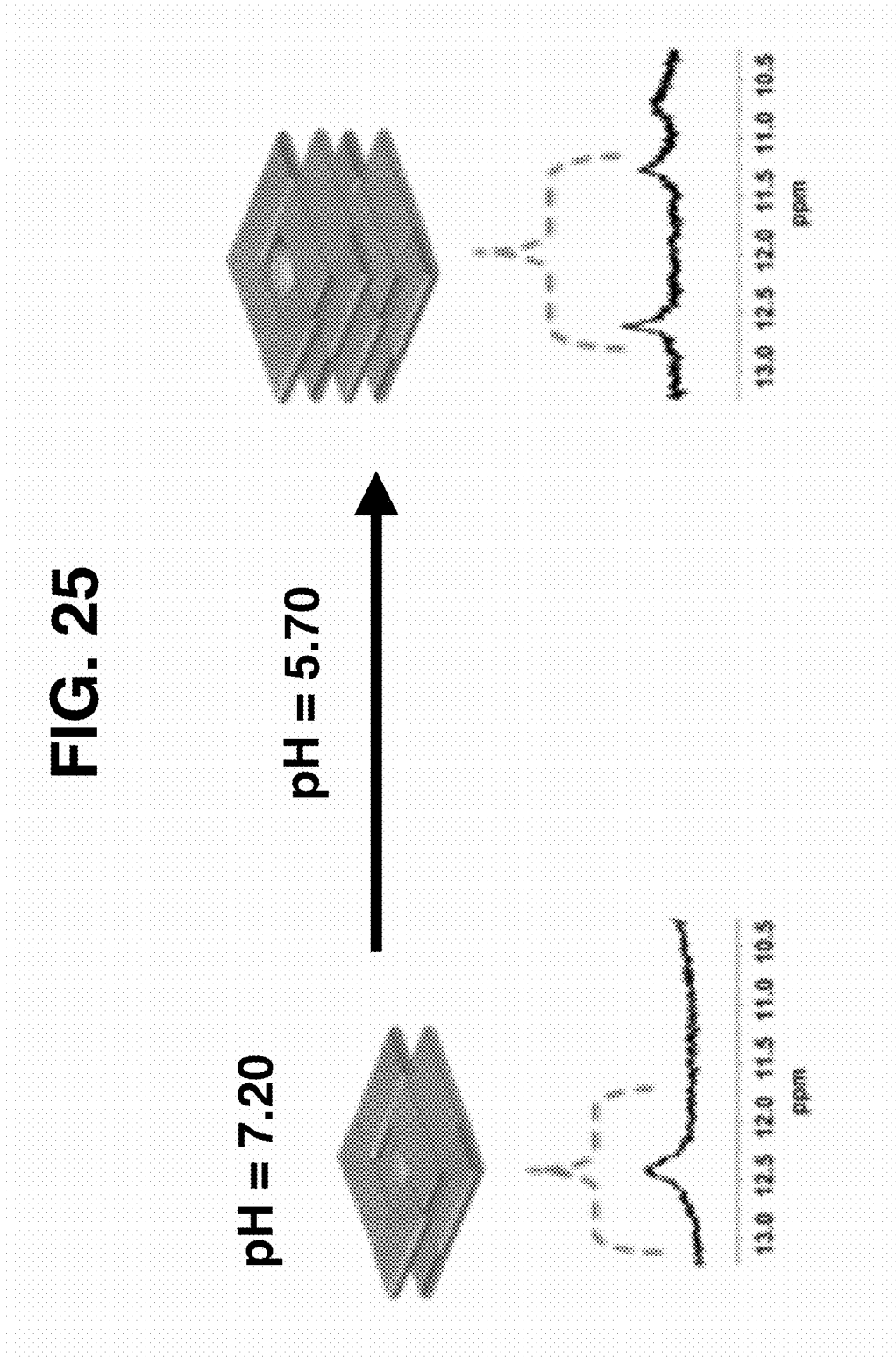
FIG. 25 illustrates the isothermal disassembly process of dual-responsive f-SHS, according to an embodiment of the present invention.

As shown in FIG. 25, the isothermal disassembly process of f-SHS can be performed by decreasing from pH 7.2 to pH 5.7, just like the disassembly process of SHS by applying a stimulus of opposite magnitude (pH or temperature). This isothermal process can be achieved because imidazole-containing ImAG (ImAGpD2PH or ImAGhD2OH) has a pKa of 5.7 (previously estimated) resulting in a pH-responsive behavior of the resulting oSGQ which is the component of f-SHS. After protonation of the imidazole functional groups in oSGQ below the transition pH 5.7, the protonated supramolecule switches its assembly to water-soluble hSGQ promoting the isothermal disassembly process of f-SHS.

The isothermal disassembly process can be observed once the cloudy colloidal suspension becomes completely soluble after acid titration from pH 7.2 to pH 5.7. But the disassembly process can also be followed with $^1$H NMR by comparing the NH region where the characteristic NH peak of neutral nanoglobular octameric oSGQ (which is the component of microglobular SHS) appears, with the characteristic peaks of the resulting water-soluble nanoglobular hexadecameric hSGQ. This isothermal pH-responsive behavior is a convenient method to release encapsulated cargo for delivery applications. FIG. 25 shows $^1$H NMR (500 MHz, 25.7° C.) at pH 7.20±0.01 in which f-SHS are composed of oSGQ (5 mM of f-SHS in $H_2O-D_2O$ (9:1) and 2 M KI) and $^1$H NMR (500 MHz, 25.7° C.) after f-SHS is disassembled at pH 5.70±0.01 in water-soluble hSGQ (0.455 mM of f-SHS in $H_2O-D_2O$ (9:1), 181 mM KI).

Figure 26:
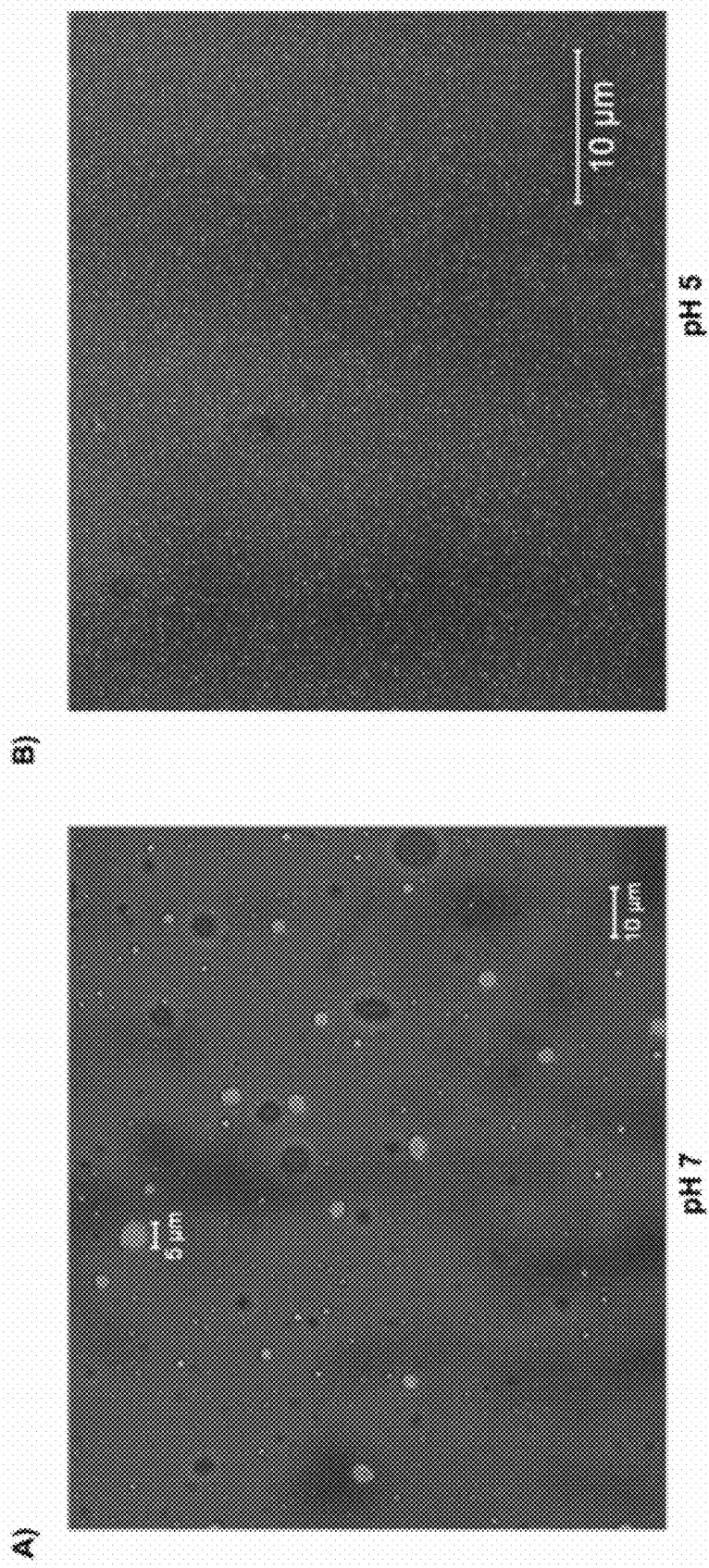
FIG. 26 shows confocal microscopy images of SHS, according to an embodiment of the present invention.

Biorelevant pH- and thermo-responsive properties of the resulting SGQ formed by ImAGpD2OH (or ImAGhD2OH) makes this derivative an excellent means for encapsulation applications. Encapsulation of the anticancer drug doxorubicin (DOX) by thermoresponsive SGQ that self-assembled at 32° C. into microglobules was previously reported. Now, the present invention provides encapsulation studies of DOX with oSGQ by pH-induced encapsulation as shown in FIG. 26, which shows confocal microscopy images of SHS at A) 8% DOX at pH 7 and B) 10% at pH 5 (5 mM of ImAGpD2OH, 2 M KI, 0.172 mM of DOX, 25° C.). At 25°

C. and pH 7, DOX is encapsulated within the microglobules composed of oSGQ, but at pH 5, hSGQ go to solution by releasing the DOX.

Slow Controlled Release

In addition to the ability of f-SHS to encapsulate different types of guests and their potential use as imaging probes, the guest-release properties are also explained. The guest leakage of non-encapsulated guest for the samples was evaluated by measuring the aqueous phase by UV-Vis spectroscopy. However, the amount of non-encapsulated guest leakage in the aqueous phase was below the detection limit of the instrument (less than 1 µM). For that reason, the present invention was focused in the DOX release with time by increasing the equivalents of encapsulated DOX in the f-SHS.

Figure 27:
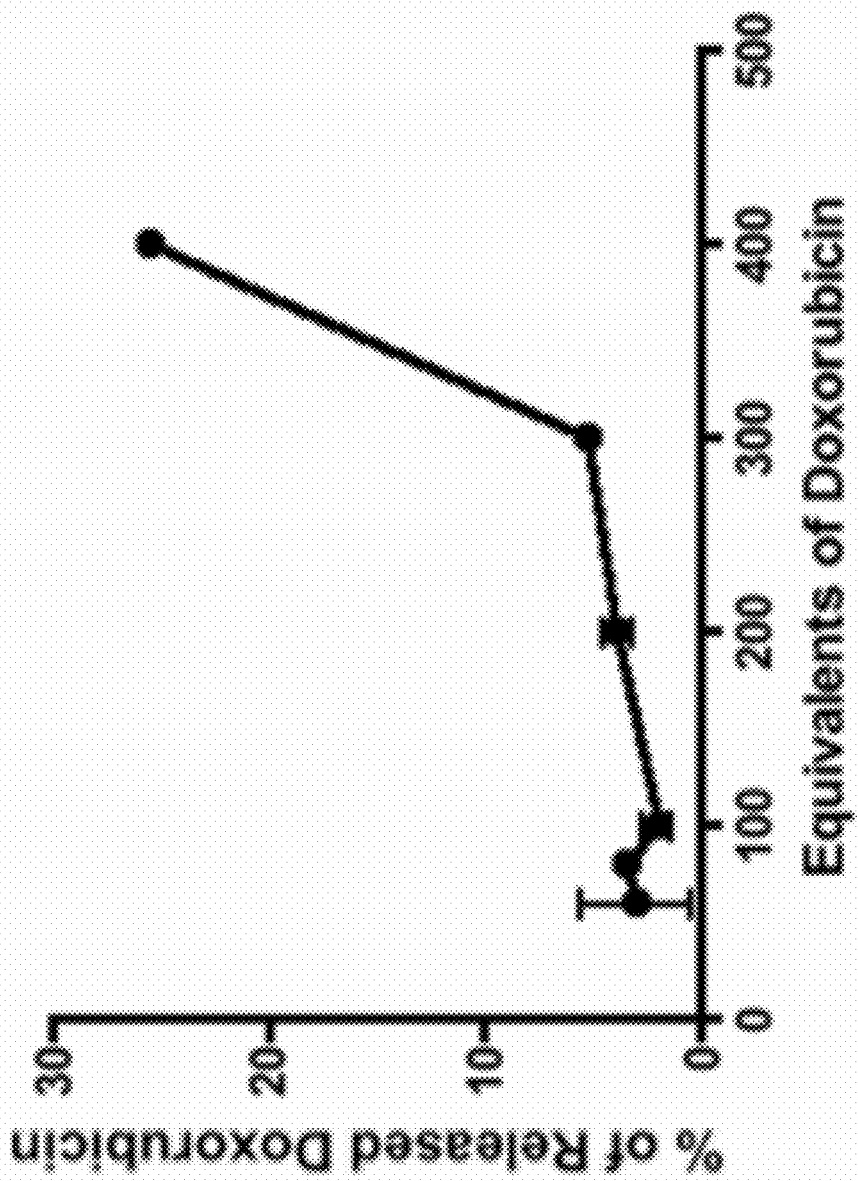
FIG. 27 shows the percentage of released DOX detected in the aqueous phase at pH 7.2 during 5 min of incubation after the encapsulation of different equivalents of DOX in the f-SHS, according to an embodiment of the present invention.

Six different 150 µL solutions of 5 mM SHS were prepared and placed in a water bath at 40° C. To each of these solutions, different equivalents of DOX were loaded to obtain solutions with 60, 80, 100, 200, 300, and 400 equivalents of DOX. It should be noted that to prepare these samples, different volumes of a 487 µM solution of DOX were added, so that the resulting concentration of SHS was not the same in each of the solutions. However, since the same initial volume of SHS was used, the amount of moles in solution is constant. To examine the encapsulation capacity of the microglobules, the solutions were fixed by adding them dropwise to a vial containing 1 mL of 1×PBS buffer to form two phases. An aliquot was obtained from the aqueous phase to determine the amount of non-encapsulated DOX in solution by UV-Vis as shown in FIG. 27, which indicates the percentage of released DOX detected in the aqueous phase at pH 7.2 during 5 min of incubation after the encapsulation of different equivalents of DOX in the f-SHS (0.833 mM of f-SHS, 333 mM KI, 60, 80, 100, 200, 300 and 400 Equiv DOX 487 µM). This experiment was performed to have an idea of the amount of DOX leakage from the colloidal phase of f-SHS to perform the time-release experiments of FIG. 28 in which 100 Equiv. DOX ware selected for the studies. To perform this experiment, the amount of DOX detected in the aqueous phase (PBS) was measured after 5 min at pH 7.2 and 40° C. It is assumed that the DOX detected in the aqueous phase came from the colloidal phase of f-SHS. The percentage of released DOX was calculated for each point, by using the concentration of DOX detected in the aqueous phase with respect the initial maximum concentration different DOX equivalents added in the colloidal phase of f-SHS.

In contrast to other delivery vehicles that release their guest prematurely, f-SHS showed a slow-release behavior that is very convenient for drug-delivery applications. According with the performed UV-Vis studies, f-SHS has great affinity for DOX but the attractive feature is that the encapsulated cargo can be released to the aqueous phase outside the colloidal phase of f-SHS. For in vivo applications, it is necessary that this kind of guest reaches the target tissue without affecting other surrounding tissues. Many NPs are limited to covalent chemistry to retain their encapsulated guest, but with f-SHS a system is provided that can survive higher dilutions without losing the non-covalent encapsulated cargo.

Figure 28:
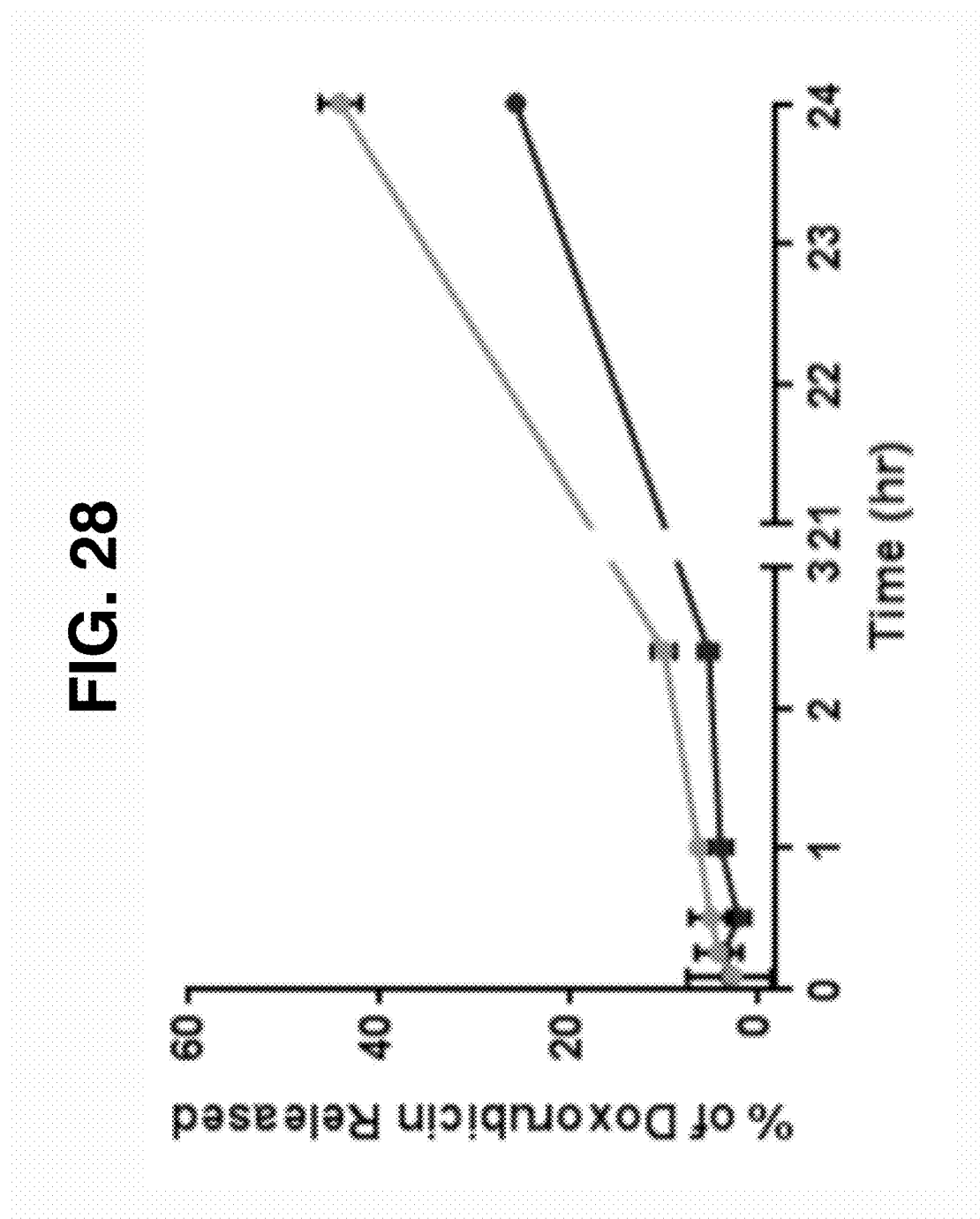
FIG. 28 shows the percentage of encapsulated DOX released from f-SHS to the aqueous phase as a function of time and pH, according to an embodiment of the present invention.

For the time-release experiments, 100 µL of SHS colloid were added to a 7 mL scintillation vial at 40° C. containing 1 mL of PBS at pH 7.2 or sodium acetate buffer at pH 5. For both pH 5 and 7.2, six samples were prepared containing the two phases (colloidal and aqueous non-colloidal) to measure the concentration of non-encapsulated and released DOX in the aqueous (non-colloidal) phase from the f-SHS colloidal phase. 100 µL of the aqueous phase were extracted at different time points (5 min, 15 min, 30 min, 60 min, 146 min and 24 h) to be analyzed by UV-Vis as shown by FIG. 28, which indicates the encapsulated DOX released from f-SHS to the aqueous phase as a function of time at pH 5.00±0.01 (orange) and pH 7.20±0.01 (blue) at 40.0° C. In this graph, the percentage of detected DOX in the aqueous phase (PBS) that was measured by UV-VIS at 480 nm is represented. It is assumed that the detected DOX in this aqueous phase was from the colloidal phase of f-SHS. The percentage of DOX was calculated by normalizing the concentration of DOX detected in the aqueous phase with the original concentrations (487 µM) of DOX added (100 Equiv.) to the colloidal phase (0.833 mM of f-SHS, 333 mM KI). Note that at pH 5.00±0.01 and 40.0° C., the f-SHS is not disassembled in hSGQ as in FIG. 26 because those conditions promote the formation of f-SHS that is composed of hSGQ and for that reason not all the DOX is released at pH 5.00±0.01.

Figure 29:
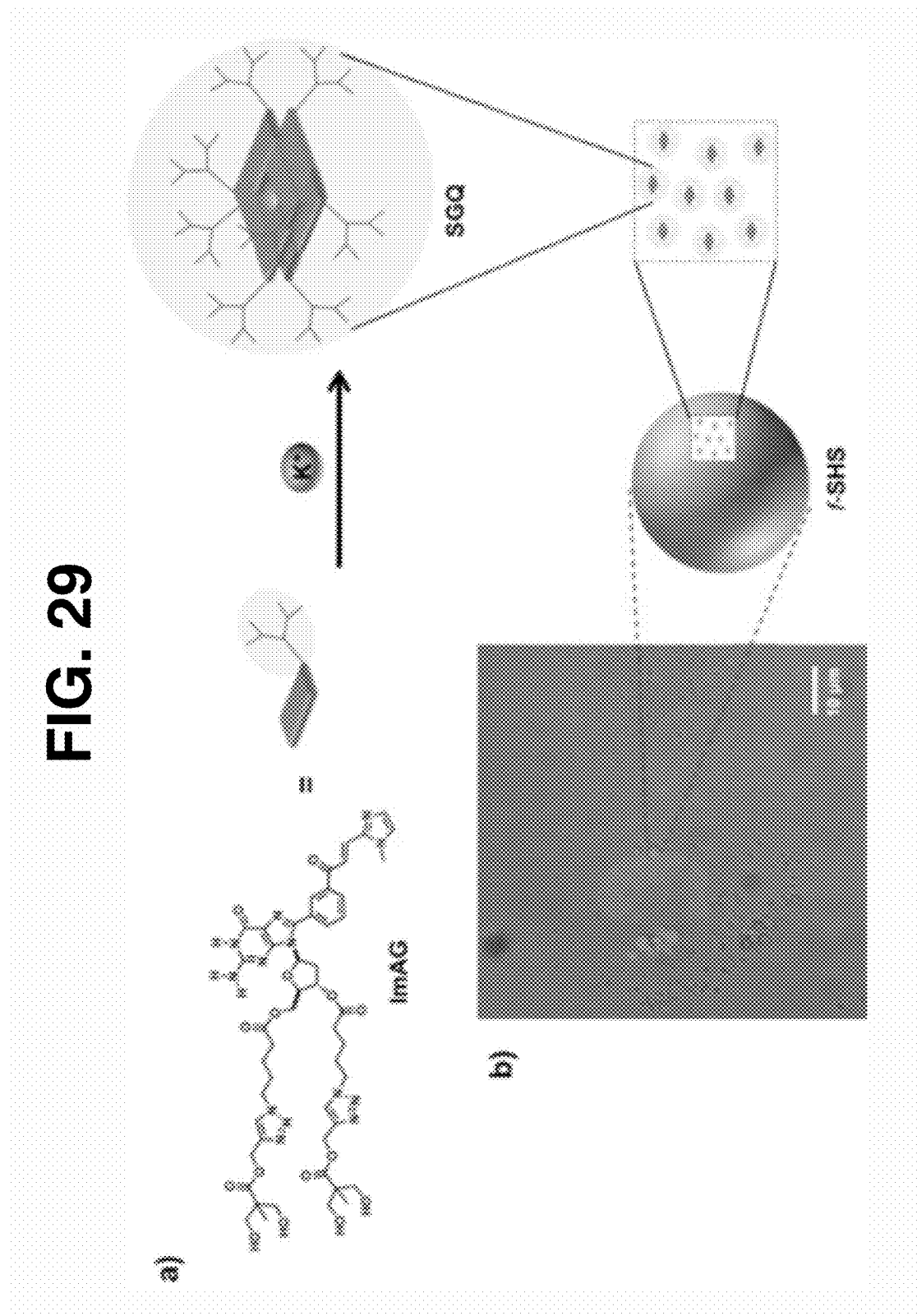
FIG. 29 illustrates the formation of f-SHS made from ImAGpD2OH and its cellular uptake into neuroblastoma cells, according to an embodiment of the present invention.

The f-SHS are Biocompatible (Non-Cytotoxic) Particles that are Taken Up by Neuroblastoma Cancer Cells (SH-SY5Y) In Vitro, which Make them Suitable as Probes for Biological Studies We discovered that f-SHS could be internalized in neuroblastoma cells (SH-SY5Y; the most common extracranial solid cancer in children), enabling the development of new biological probes as illustrated in FIG. 29. Cell internalization was observed without the need of permeabilization agents, invasive microinjection techniques, or surface modifications with fusogenic groups that help fusion with cell membranes. The f-SHS made from ImAGpD2OH needs no further surface modifications to promote their cellular uptake (a common strategy previously reported), which is a critical factor for using the f-SHS for drug- and gene-delivery applications.

Figure 30:
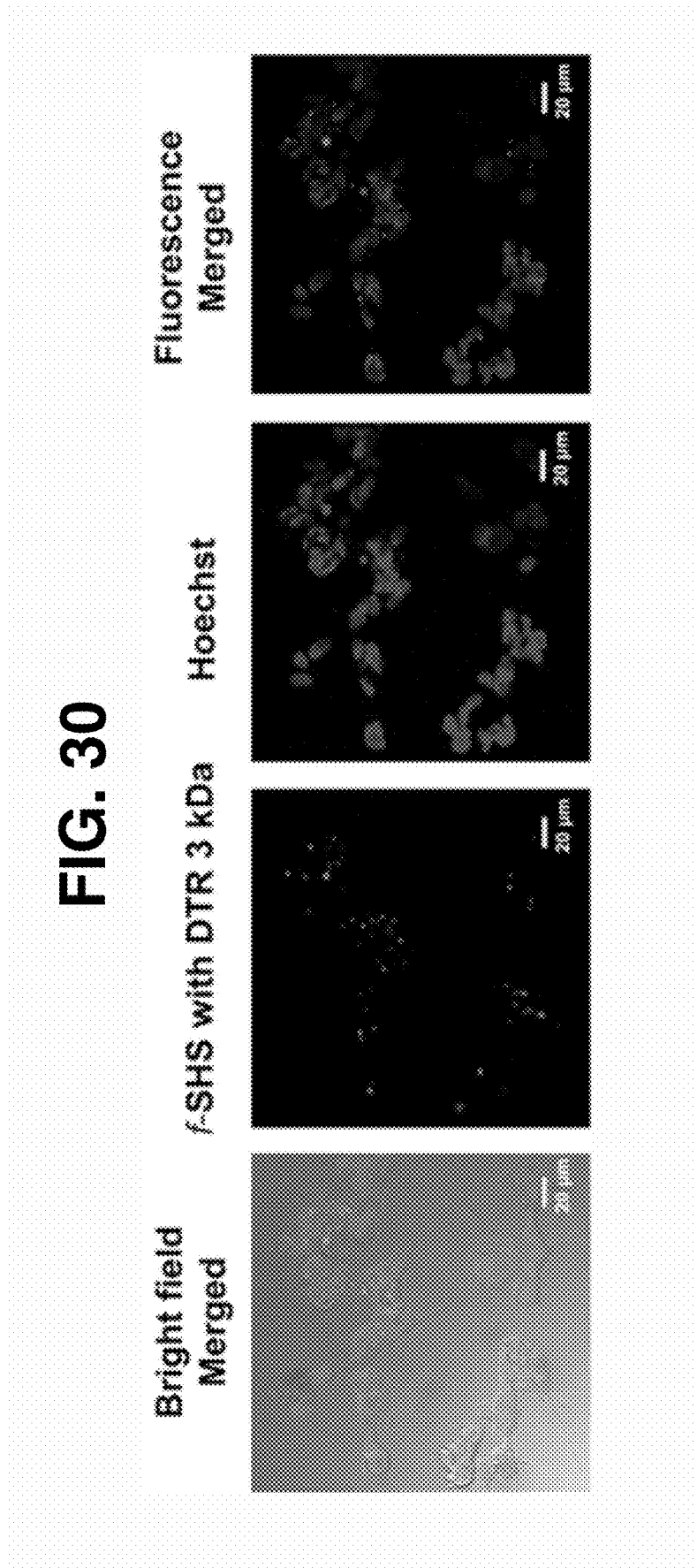
FIG. 30 shows CLSM images of SH-SY5Y neuroblastoma cells in presence of f-SHS loaded with Dextran Texas Red, according to an embodiment of the present invention.

Encapsulation of dextran labeled with Texas Red of 3 kDa (DTR-3) into f-SHS is a convenient strategy to prepare fluorescent biological probes because it does not require further covalent modifications to keep the fluorescent guest encapsulated inside the f-SHS. For example, a 24 h incubation study of SH-SY5Y cells with f-SHS@DTR-3 demonstrated that the cellular uptake of these cells was reproducible as shown in FIG. 30, which provides CLSM images of SH-SY5Y neuroblastoma cells in presence of a) f-SHS loaded with 171 µM Dextran Texas Red 3 kDa (DTR 3 kDa) after 24 h of incubation. The red channel (561 nm) was used to measure f-SHS@DTR-3 particles, while the blue channel (405 nm) was used to measure the cell nuclei stained with the Hoechst dye. Moreover, the amount of f-SHS@DTR-3 increased significantly after incubation for 24 h, relative to the same experiment after incubation for 12 h, which underscores the relationship between incubation time and the amount of internalized particles. Further confirmation of cellular uptake comes from flow cytometry measurements, which also indicate selectivity between different types of cells (data not shown).

Cell Culture Method

SH-SY5Y and HEK-293 cell lines were purchased at ATCC. SH-SY5Y cells are a thrice-cloned line obtained from a metastatic bone marrow tumor of a human female. DAPI nuclear stain used was the kit VECTASHIELD mounting medium from VECTOR laboratories. In the case of Hoechst 33342 (Hoechst) nuclear stain; a kit called "NucBlue Live Ready Probes Reagent" from Life Technologies, Inc. was used (Lysotracker kit was also obtained from Life Technologies, Inc.). The rest of the reagents for the cell culture treatments were purchased from Aldrich and used without further treatment.

Both cell lines were cultured in Dulbecco's Eagle's Medium/Nutrient Mixture F-12 (DMEM F-12), that was supplemented with 10% fetal bovine serum (FBS) (from Aldrich), 100 units/mL of penicillin, 100 µg/mL of streptomycin and 0.25 µg/mL of amphotericin B. Cells were incubated in humidified air containing 5.0% $CO_2$ at 38.0° C. Cells were placed in wells at $1\times10^6$ per well in a 48 well plate (1.0 mL). The cell media (pH=7.4) were the cells were cultured was changed the next day, and every two days after that.

b) Fluorescence Confocal Microscopy

The confocal microscopy images were performed in a Confocal Zeiss LSM 510 META on an Axiovision Z1 microscope with an excitation range of (514-515) nm and emission range of (565-615) nm from the Confocal Microscopy Facility at the University of Puerto Rico (CIF-UPR). The microscope objectives used to obtain the confocal images were Plan-Apochromat 63×/1.40 Oil DIC M27 and EC Plan-Neo Fluar 40×/0.75. Laser wavelength excitation wavelengths were 561 nm (for f-SHS, DOX and DTR 3 kDa), 405 nm (for DAPI and Hoechst) and 633 nm (for Lysotracker). The emission filters used are 588-738 for ChS1, BP 420-480 for Ch2 and BP 575-615 IR for Ch3. ChS1 of 652-738 was used for Lysotracker and Ch3 of LP 575 was used for incubation experiments of 8 days. All the fluorescence confocal microscopy images, z-stacks and movies were processed in Zeiss LSM Image Browser software The f-SHS Particles are a Viable Drug Delivery System as Demonstrated by the (In Vitro) Delivery, and Controlled Release, of the Anticancer Drug DOX into Neuroblastoma Cancer Cells.

Figure 31:
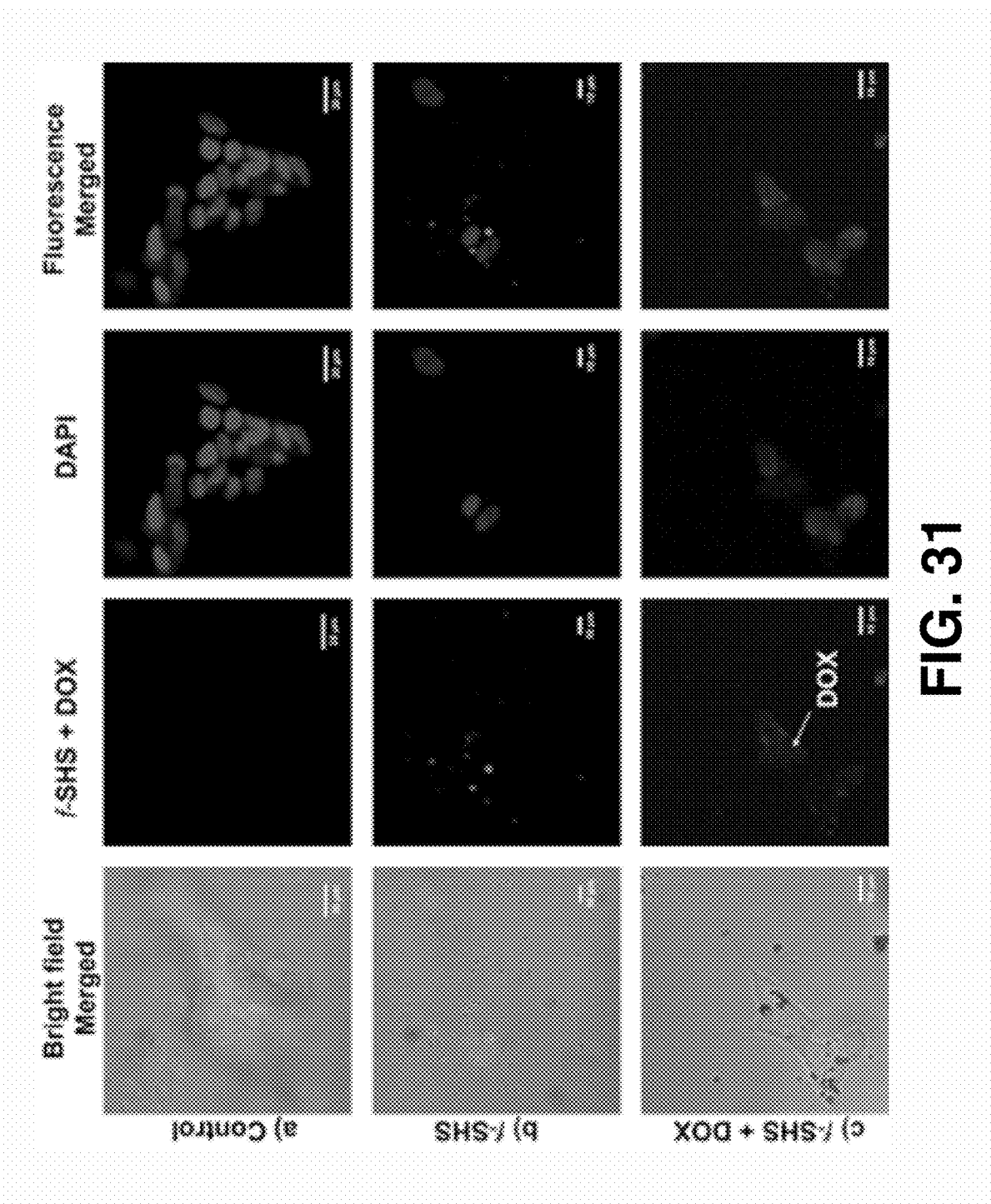
FIG. 31 shows CLSM images of various neuroblastoma (SH-SY5Y) cells, according to an embodiment of the present invention.
Figure 32:
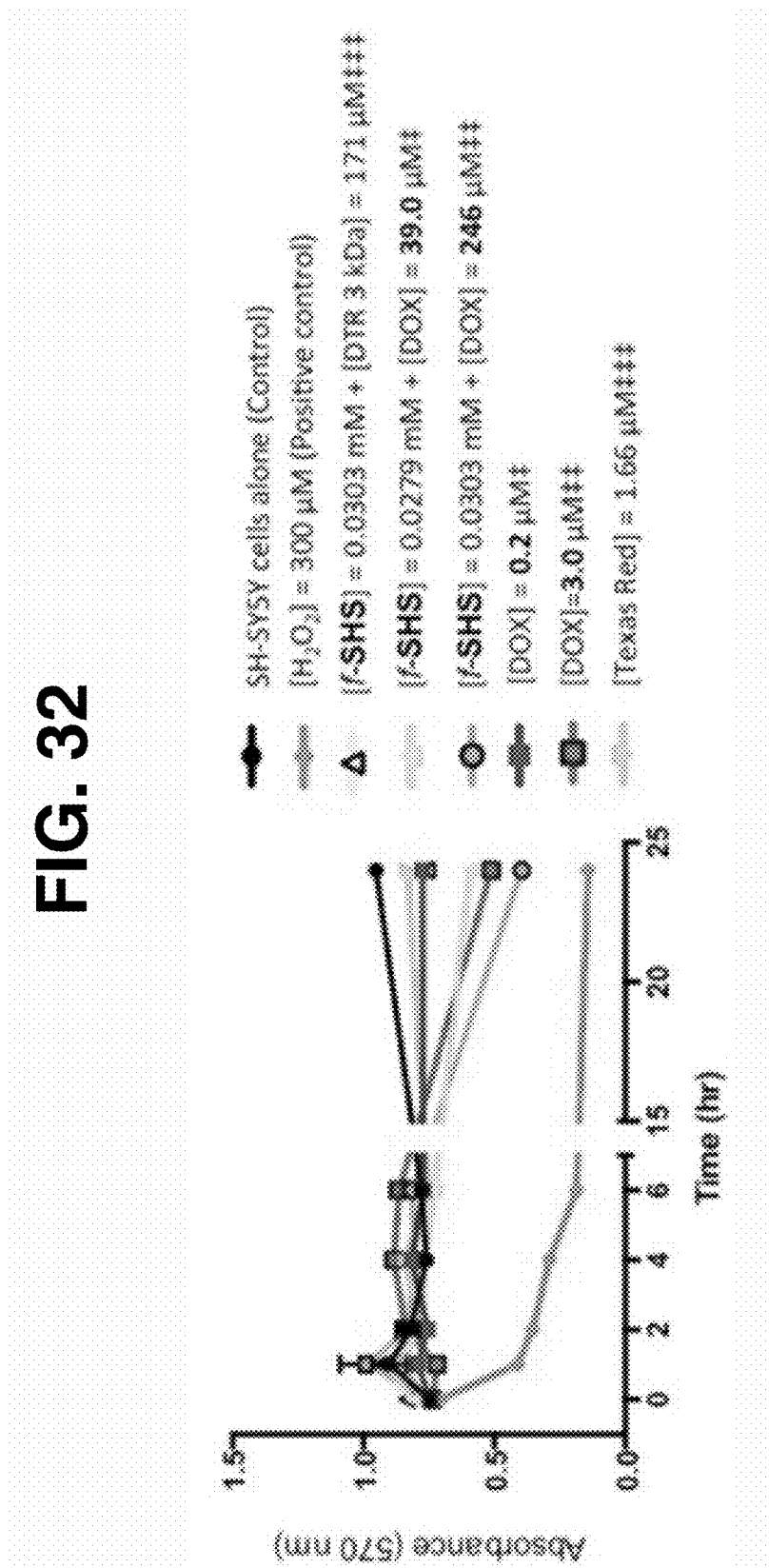
FIG. 32 shows an Absorbance vs. Time plot for MTT viability assay of neuroblastoma (SH-SY5Y) cells with various concentrations of DOX and f-SHS@DTR-3, according to an embodiment of the present invention.

The evidence from the CLSM experiments shown in FIG. 31, indicate that the f-SHS particles are suitable delivery systems for the anticancer drug DOX, given the cellular uptake of the f-SHS@DOX particles and the controlled release of DOX. FIG. 31 shows CLSM images of neuroblastoma (SH-SY5Y) cells: (a) with no f-SHS or DOX added (control); (b) with "empty" f-SHS particles; and (c) with f-SHS@DOX particles (f-SHS loaded with 35.9 µM DOX) after incubating for 12 h. The red channel (561 nm) was used to detect both the f-SHS, f-SHS@DOX, and DOX, while the blue channel (405 nm) was used to detect the cell nuclei stained with the DAPI dye. Furthermore, analysis of the CLSM images after 24 h reflects a decrease in the population of the neuroblastoma (SH-SY5Y) cells and the concomitant increase of apoptotic bodies resulting from cells undergoing apoptosis (i.e., dying cells). However, it is important to confirm these observations with an alternative experimental protocol that provides quantitative information regarding the cell viability and cytotoxicity in the presence of the f-SHS particles with and without DOX. For these purposes, we used the commercially available MTT (3-[4, 5-dimethylthiazol-2-yl]-2,5 diphenyl tetrazolium bromide) assay (FIG. 32). The MTT assay is a colorimetric viability assay where the reduction of the water-soluble MTT dye is metabolized by the SH-SY5Y cells into a purple (formazan) product whose concentration is proportional to the population of viable cells. Proper precautions were taken to ensure that the measured effects originated from the f-SHS@DOX particles and not from extraneous traces of DOX. This was achieved by washing the colloidal phase of the f-SHS@DOX particles with PBS.

The MTT assay confirmed the non-toxicity (for the concentration range tested) of the f-SHS, in contrast to other reported systems that need modifications to reduce toxicity. The f-SHS@DOX particles loaded with relatively large amounts of DOX show lower toxicity, in the short term relative to similar concentrations of DOX alone (e.g., 0.2 µM DOX is cytotoxic; f-SHS@DOX with 39.0 µM DOX is less cytotoxic; f-SHS@DOX with 246 µM DOX kills 50% of the cancer cells after 24 h). Due to the controlled sustained release, the invention has the same cytotoxic effect in the long run as shown in FIG. 32, which illustrates the MTT viability assay of neuroblastoma (SH-SY5Y) cells for 24 h with various concentrations of DOX and f-SHS@DTR-3. The results of two control experiments with SH-SY5Y cells were also included for comparison: alone (negative control) and a sample to which $H_2O_2$ (300 µM; positive control) was added. Interestingly, even DTR-3 shows some cytotoxicity at the concentrations used, but this detrimental biological activity is prevented by encapsulation in the f-SHS particles. This is an attractive feature of drug delivery systems since the delayed toxicity will prevent detrimental side effects due to toxicity in normal cells.

MTT Assay Protocol

These experiments were performed using an MTT Cell Proliferation Assay purchased from ATCC. First, cells were placed in wells at $1\times10^6$ per well in a 96 well plate (100 µL). They were left there for 24 h until cells adhered to the plate. When 80%-90% of confluence was reached, the cells were treated at different time points with the performed treatments including the positive control of 300 µM $H_2O_2$. After treatment, 100 µL of fresh medium per well were added, followed by 10 µL of MTT reagents. Cells were then incubated for 8 h or overnight with the reagent until a precipitate was visible. Next, 100 µL of detergent reagent were added to the sample, without removing any of the medium. Then the treated cells were left at 25° C. in the dark for 4 h to measure the absorbance at 570 nm excitation wavelength.

The f-SHS as a Viable Transfection Agent, Suitable for Gene-Delivery Applications Another attractive feature of the f-SHS particles is their potential as a versatile platform technology for delivering nucleic acid therapeutics. As described earlier the f-SHS particles can encapsulate short DNA oligonucleotides (FIG. 24). Delivery of short DNA oligonucleotides (oDNA) is useful for small interfering RNA (siRNA), microRNA (miRNA), aptamers, etc. The present invention demonstrates the potential for complexation and cell delivery of circular plasmid DNA. Transfection of a gene into neuroblastoma cells would open the possibility of using the f-SHS particles as gene delivery agents. Gene delivery agents in turn are versatile systems for the treatment of rare monogenetic diseases (i.e., gene therapy), cancer, infectious diseases (e.g., DNA vaccines) and other diseases.

Figure 33:
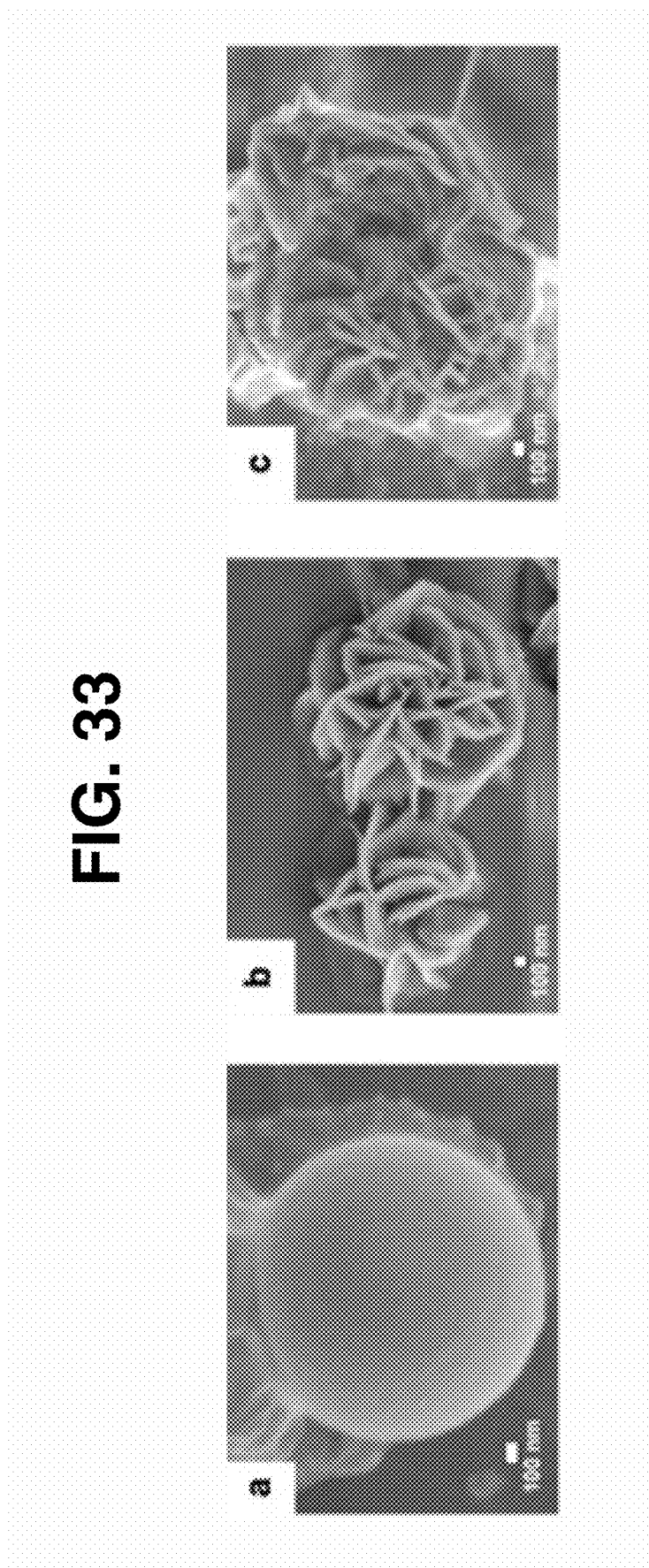
FIG. 33 shows scanning electron microscopy (SEM) images of: f-SHS, f-SHS@pCri and f-SHS@pGFP, according to an embodiment of the present invention.

Considering the significant difference in size between DNA oligonucleotides and pDNA, we needed to confirm the interactions between the latter and f-SHS particles. Incubation of f-SHS particles and two different pDNAs encoding for green fluorescent protein (pGFP) and crimson fluorescent protein (pCri), this was followed by drop-casting (depositing a drop on a surface and letting it air dry at 36° C.). Scanning electron microscopy (SEM) images of the samples reveal a dramatic morphological transformation as shown in FIG. 33. While the f-SHS particles are spherical, the complexes f-SHS@pGFP and f-SHS@pCri adopt flower-like morphologies (these types of particles are referred as nanoflowers). We believe that the f-SHS particles serve as a template onto which the pDNA form nanocrystalline domains (i.e., petals) guided by non-covalent interactions.

Figure 34:
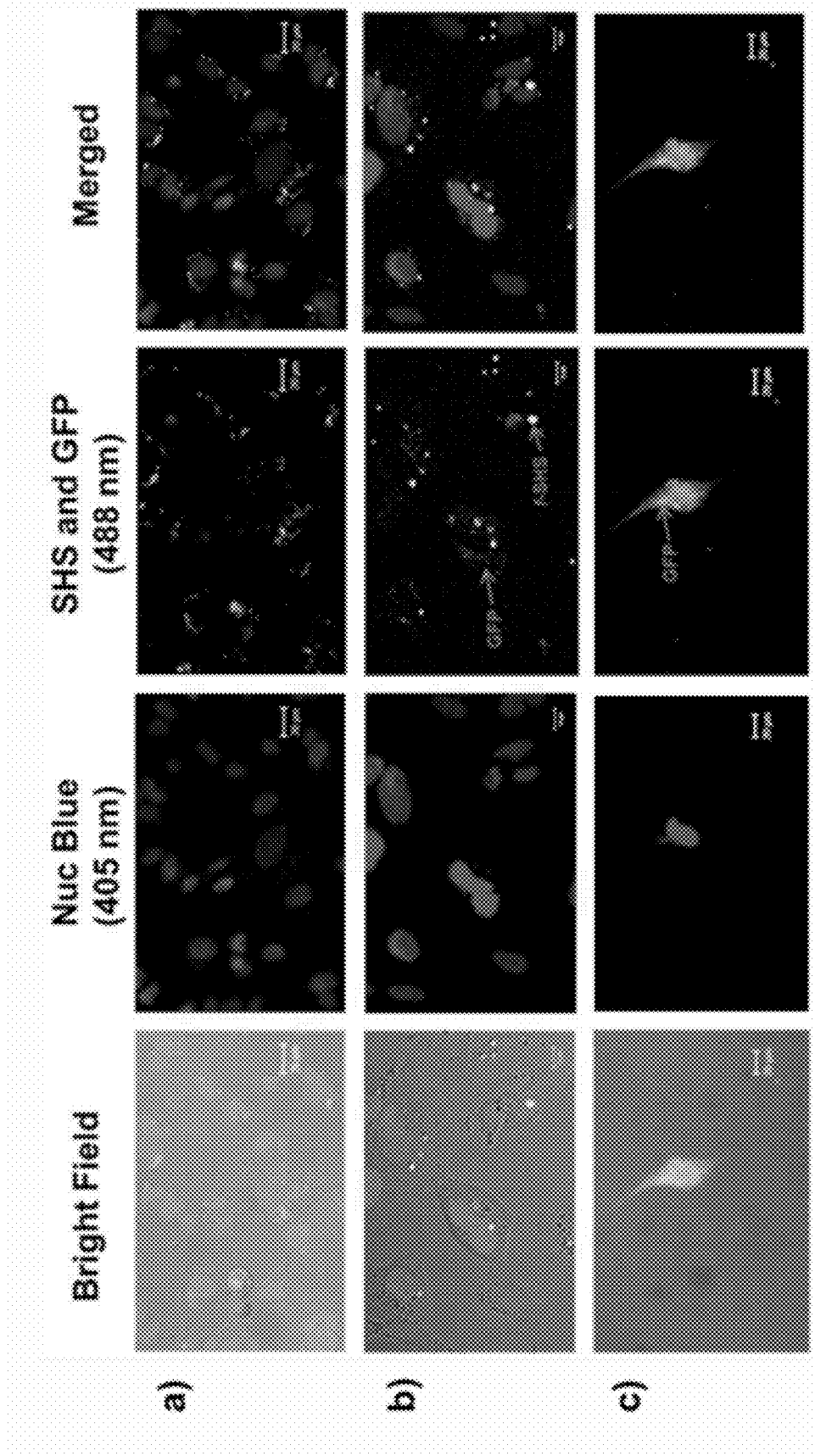
FIG. 34 shows CLSM images of SH-SY5Y cells transfected with pGFP, according to an embodiment of the present invention.
Figure 35:
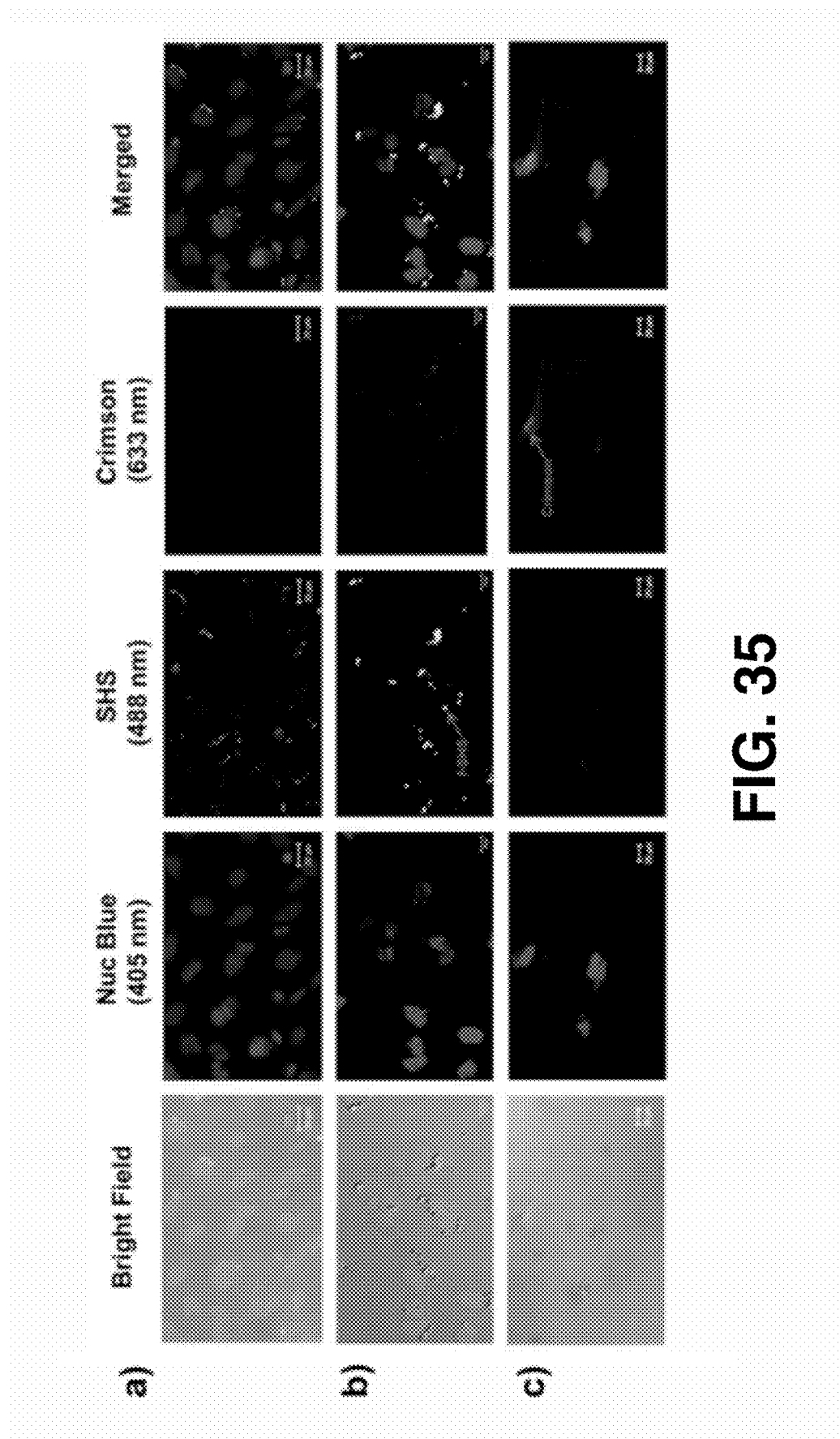
FIG. 35 shows CLSM images of SH-SY5Y cells transfected with pCri, according to an embodiment of the present invention.

CLSM measurements confirm that both, f-SHS@pCri and f-SHS@pGFP particles are also taken up by neuroblastoma (SH-SY5Y) cells. FIG. 34 shows CLSM images of SH-SY5Y cells transfected with pGFP (the cell nuclei was stained with the Nuc Blue dye). Images taken after incubation of SH-SY5Y cells with: (a) f-SHS; (b) f-SHS@pGFP; and (c) LA2000@pGFP. All the incubation experiments were performed at 37° C. and 5% $CO_2$ without movement for 8 days. FIG. 35 shows CLSM images of SH-SY5Y cells transfected with pCri (the cell nuclei was stained with the Nuc Blue dye). Images taken after incubation of SH-SY5Y cells with: (a) f-SHS; (b) f-SHS@pCri; and (c) LA2000@pCri. All the incubation experiments were performed at 37° C. and 5% $CO_2$ without movement for 8 days. As previously explained, the resulting transfected cells, were incubated for 8 days, after which time expression of both proteins was detected by CLSM measurements. Negative control experiments indicated that none of these pDNAs are internalized in the cells by themselves. Positive control experiments with the commercially available transfection agent LIPOFECTAMINE™ 2000 (LA2000) also lead to the expression of both proteins as shown in rows (c) of FIGS. 34 and 35. An experiment with two different pDNAs provides confirmation that the f-SHSs are a suitable transfection platform (independent of the gene sequence). Furthermore, since there is some overlap between the inherent emission of the f-SHS particles and that of GFP (both emit in the range measured by the 488 nm channel in fetal bovine serum), the experiments with Cri, with emission detected in at 633 nm channel, confirmed that they were the measured fluorescence results from the protein expression. An important observation is that while the cells treated with LA2000 (rows (c) of FIGS. 34 and 35) showed signs of meaningful cytotoxicity (e.g., a lower cell density and the presence of cell debris), the corresponding experiments where f-SHS was used, showed the presence of numerous and healthy looking cells (indicating their negligible cytotoxicity).

The distribution of the expressed protein is different in experiments with LA2000, f-SHS@pGFP and f-SHS@pCri as shown in rows (b) of FIGS. 34 and 35. While the first two show a wide cytoplasmic distribution (with LA2000 showing a wider fluorescence distribution of all), the f-SHS@pCri leads to a more localized expression sites, colocalizing with the f-SHS particles as shown in rows (b) of FIG. 35.

Procedure to Perform Plasmid Transfection Studies with f-SHS

A volume of 300 µL of each f-SHS@plasmid was added to corresponding wells. In the case of LIPOFECTAMINE™ sample, only 100 µL of each preparation were added to each well. For each individual plasmid control sample, these volumes were added to each well: 20 µL of p-E2Crimson and 30 µL of p-GFP. All cells samples were incubated for 15 h at 37° C. and 5% $CO_2$ without movement as a first checkpoint of behavior. Then, the incubation of cells was continued at 37° C. for 3 and 8 days. After each checkpoint, confocal microscopy images were taken to visualize or analyze the current encapsulation/intake/protein expression effect. Two additional samples were prepared to be evaluated at Day 3 checkpoint: 0.164 mM ImAG at pH 6.1 encapsulating 10 µL of p-GFP; and 0.164 mM ImAG at pH 6.1 encapsulating 15 µL of p-E2Crimson. Samples were prepared individually for the three different checkpoints to avoid contamination during their management and transport to the confocal microscopy facilities. (Confocal Zeiss LSM 510 META on an Axiovision Z1 microscope from the Confocal Microscopy Facility at the University of Puerto Rico (CIF-UPR)).

While the embodiments of the present invention have been showed as described, various alterations can be made without deviating from intended utility; and all such modifications are intended to be covered within this patent.

We claim:
1. A method of synthesizing a cluster of self-arranged supramolecular structures comprising:
  mixing KI salts with a phosphate buffer solution (PBS) and molecules with the chemical structure (I),

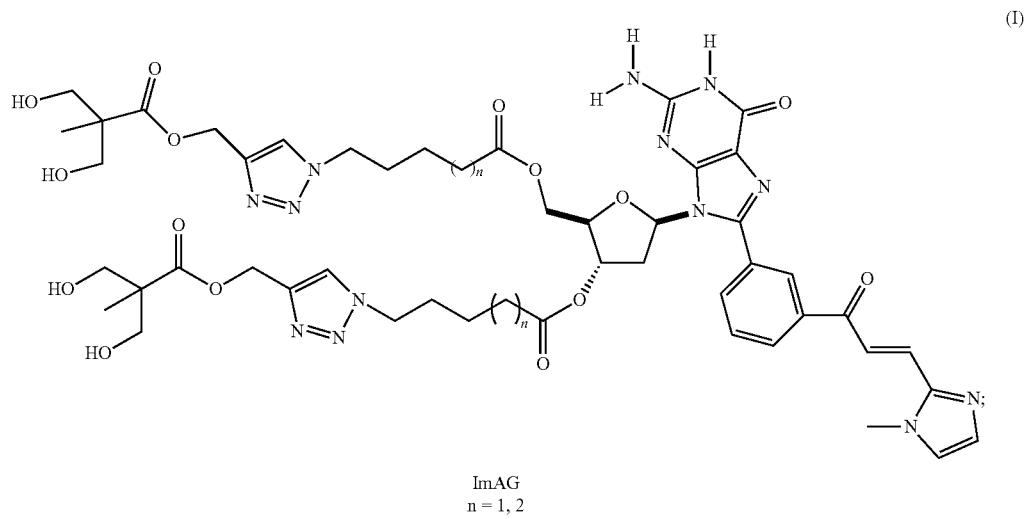

ImAG
n = 1, 2 allowing dissolution of said molecules in the (PBS) effectively forming supramolecular structures;
  removing said supramolecular structures from said mixture and diluting said removed supramolecular structures in PBS without KI salt to lower the ionic strength, effectively fixing together said supramolecular structures; and inducing the fixed supramolecular structures to form a cluster of self-arranged supramolecular structures.

2. The method of claim 1, wherein said KI salts and said molecules are mixed together prior to mixing with said (PBS).

3. The method of claim 1, wherein said mixture is cooled for an amount of time sufficient to allow complete dissolution of said molecules in the (PBS).

4. The method of claim 1, wherein said mixture has a neutral pH.

5. The method of claim 1, wherein said mixture has an acidic pH.

6. The method of claim 4, wherein each of said supramolecular structures comprises 8 subunits of said molecules.

7. The method of claim 5, wherein each of said supramolecular structures comprises 16 subunits of said molecules.

8. The method of claim 1, wherein said supramolecular structures are induced to form said cluster of self-arranged supramolecular structures by subjecting said supramolecular structures to a temperature equal to or greater than a transition temperature.

9. The method of claim 8, wherein the pH of said mixture is neutral.

10. The method of claim 8, wherein the pH of said mixture is acidic.

11. The method of claim 8, wherein said transition temperature is about 8-15° C.

12. The method of claim 8, wherein said transition temperature is about 42-50.5° C.

13. The method of claim 8, wherein said transition temperature is about 4-5.5° C.

14. The method of claim 8, wherein said transition temperature is about 29-59.3° C.

15. The method of claim 1, wherein said mixture is cooled at a temperature below said transition temperature.

16. A method of encapsulating a guest material inside a cluster of self-arranged supramolecular structures, said method comprising:

mixing a guest material with KI salts, phosphate buffer solution (PBS) and clusters of self-arranged supramolecular structures, wherein said clusters of self-arranged supramolecular structures are diluted in PBS in the absence of KI salt for fixing said clusters of self-arranged supramolecular structures by lowering the ionic strength prior to mixing with said guest material, each supramolecular structure comprises a plurality of molecules of the chemical structure:

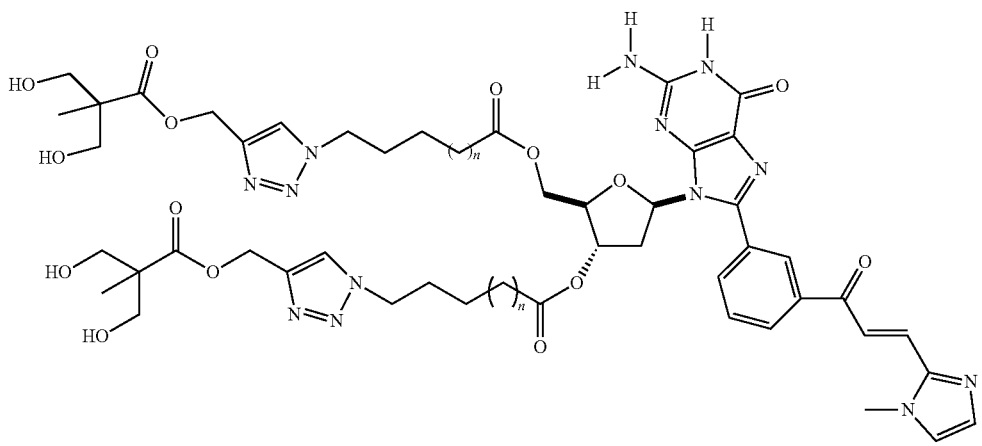

ImAG
n = 1, 2 and agitating said mixture for an amount of time sufficient to allow said guest material to diffuse through said clusters of fixed self-arranged supramolecular structures, effectively encapsulating said guest material inside the clusters of fixed self-arranged supramolecular structures.

17. The method of claim 16, wherein said guest material is in solid state.

18. The method of claim 16, wherein said guest material is in liquid state.

19. The method of claim 16, wherein said guest material is a polymer.

20. The method of claim 16, wherein said guest material is a protein.

21. The method of claim 16, wherein said guest material is a molecule.

22. The method of claim 16, wherein said guest material is nucleic acid.

23. A method of releasing a guest material encapsulated inside a cluster of self-arranged supramolecular structures, said method comprising:

modifying a cluster of self-assembled supramolecular structures encapsulating a guest material, said cluster comprises supramolecular structures having a plurality of molecules of the chemical structure:

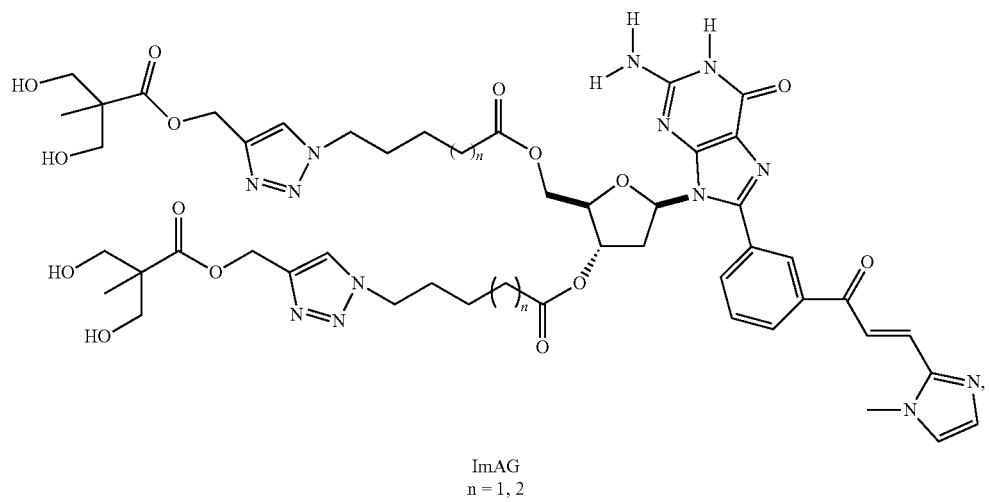

ImAG
n = 1, 2 wherein said cluster is modified by diluting said cluster in PBS in the absence of KI salt to lower the ionic strength, effectively fixing together said cluster of self-arranged supramolecular structures to allow controlled release of said guest material.

24. The method of claim 23, wherein said guest material is in solid state.

25. The method of claim 23, wherein said guest material is in liquid state.

26. The method of claim 23, wherein said guest material is a polymer.

27. The method of claim 23, wherein said guest material is a protein.

28. The method of claim 23, wherein said guest material is a molecule.

29. The method of claim 23, wherein said guest material is nucleic acid.

30. A method of releasing a guest material encapsulated inside a cluster of self-arranged supramolecular structures, said method comprising:

modifying a cluster of fixed self-assembled supramolecular structures encapsulating a guest material, said cluster comprises supramolecular structures having a plurality of molecules of the chemical structure:

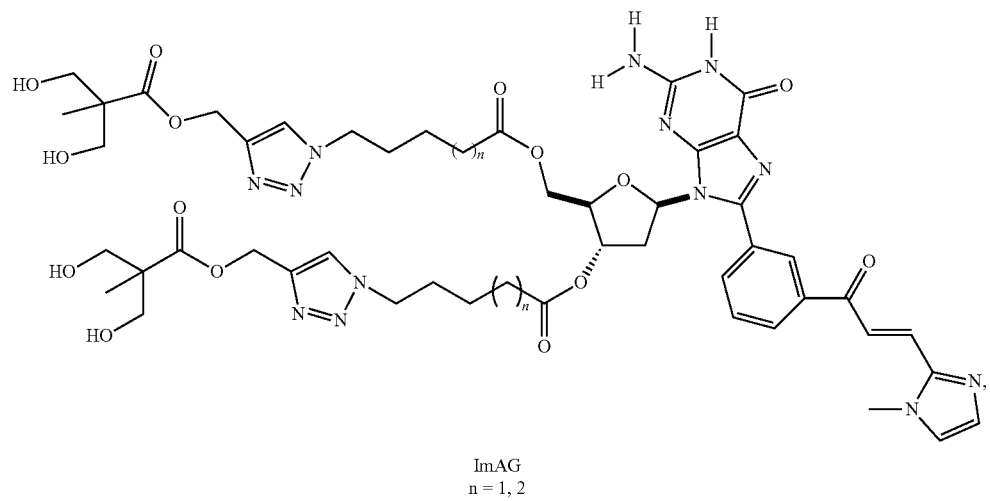

ImAG
n = 1, 2 that have been previously diluted in PBS in the absence of KI salt to lower the ionic strength, wherein said cluster is modified by subjecting said cluster to a surrounding environment having an acidic pH level, effectively disassembling said supramolecular structures to allow immediate release of said guest material.

31. The method of claim 30, wherein said guest material is in solid state.

32. The method of claim 30, wherein said guest material is in liquid state.

33. The method of claim 30, wherein said guest material is a polymer.

34. The method of claim 30, wherein said guest material is a protein.

35. The method of claim 30, wherein said guest material is a molecule.

36. The method of claim 30, wherein said guest material is nucleic acid.

* * * * *